US012599307B1

(12) United States Patent
Arool Emmanuel

(10) Patent No.: US 12,599,307 B1
(45) Date of Patent: *Apr. 14, 2026

(54) CONCURRENT MONITORING OF INDOOR OXYGEN CONCENTRATION LEVELS AND HUMAN VITAL SIGNS WITH mmWave RADAR SENSORS

(71) Applicant: Amazon Technologies, Inc., Seattle, WA (US)

(72) Inventor: Cyril Arokiaraj Arool Emmanuel, San Jose, CA (US)

(73) Assignee: Amazon Technologies, Inc., Seattle, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/914,644

(22) Filed: Oct. 14, 2024

Related U.S. Application Data

(62) Division of application No. 17/399,799, filed on Aug. 11, 2021, now Pat. No. 12,121,331.

(51) Int. Cl.
| | |
|---|---|
| *A61B 5/0205* | (2006.01) |
| *G01S 7/292* | (2006.01) |
| *G01S 13/28* | (2006.01) |
| *G01S 13/88* | (2006.01) |
| *H04B 17/318* | (2015.01) |

(52) U.S. Cl.
CPC .......... *A61B 5/0205* (2013.01); *G01S 7/2923* (2013.01); *G01S 13/282* (2013.01); *G01S 13/88* (2013.01); *H04B 17/318* (2015.01); *A61B 2560/0242* (2013.01)

(58) Field of Classification Search
CPC .......... A61B 5/0205; A61B 2560/0242; G01S 7/2923; G01S 13/282; G01S 13/88; H04B 17/318
See application file for complete search history.

(56) References Cited

U.S. PATENT DOCUMENTS

| | | | |
|---|---|---|---|
| 10,282,914 B1 * | 5/2019 | Tran ..................... | A61B 5/1036 |
| 2007/0208269 A1 * | 9/2007 | Mumford ............. | A61B 5/6803 600/595 |
| 2011/0066006 A1 * | 3/2011 | Banet ................... | A61B 5/6826 600/301 |
| 2011/0066043 A1 * | 3/2011 | Banet ..................... | A61M 1/14 600/485 |

(Continued)

*Primary Examiner* — Amine Benlagsir
(74) *Attorney, Agent, or Firm* — Eversheds Sutherland (US) LLP

(57) ABSTRACT

Technologies directed to are monitoring human vital signs with mmWave radars are described. One method sends a first signal having a first chirp that is a triangular-type chirp that increases in frequency for a first period and decreases in frequency for a second period and a second chirp that is a ramp-type chirp that increases in frequency for a third period. The method receives a second signal corresponding to the first signal. The method generates, using the first chirp and a first portion of the second signal, a third signal indicative of a human vital sign, such as a heart rate or a respiratory rate. The method measures a received signal strength indicator (RSSI) value of a second portion of the second signal at approximately 60 GHz. The method determines, using the RSSI value, a value indicative of oxygen-concentration in an ambient environment of the monitoring device.

20 Claims, 13 Drawing Sheets

(56)                    References Cited

U.S. PATENT DOCUMENTS

| | | | |
|---|---|---|---|
| 2018/0104426 A1* | 4/2018 | Oldfield | A61M 16/0006 |
| 2020/0129111 A1* | 4/2020 | Osorio | A61B 5/00 |
| 2020/0170514 A1* | 6/2020 | Hui | A61B 5/1126 |
| 2020/0297955 A1* | 9/2020 | Shouldice | A61M 16/06 |
| 2021/0000345 A1* | 1/2021 | Felix | H04Q 9/00 |
| 2021/0052844 A1* | 2/2021 | Oldfield | A61B 5/7246 |
| 2021/0125405 A1* | 4/2021 | Tran | G06T 19/20 |
| 2023/0165498 A1* | 6/2023 | Shouldice | A61B 5/168 |
| | | | 600/300 |
| 2023/0253103 A1* | 8/2023 | Dos Santos | A63B 71/0622 |

* cited by examiner

Example chirps for different phase resolutions
(vital signs monitoring)

CONCURRENT MONITORING OF INDOOR OXYGEN CONCENTRATION LEVELS AND HUMAN VITAL SIGNS WITH mmWave RADAR SENSORS

RELATED APPLICATIONS

This application is a divisional of U.S. patent application Ser. No. 17/399,799, filed Aug. 11, 2021, the entire contents of which are incorporated by reference herein.

BACKGROUND

Monitoring devices can be used to track a user's activity. Some monitoring devices are used to track a user's breathing activity and patterns while the user sleeps. The respiratory activity tracking can be used to identify sleep patterns (e.g., generate sleep scores and hypnograms) and monitor issues relating to cardiovascular or respiratory diseases or conditions. The monitoring device is typically positioned next to the user's bed (e.g., on a nightstand adjacent to the bed) and uses radar to detect movement within a detection zone to identify a respiratory waveform of the user primary user. Monitoring devices can use radar sensors to detect the range, velocity, and identity of objects in motion. Radar sensors were originally designed for military and flight applications, but have more recently been manufactured as systems-on-a-chip in smaller form factors, making them adaptable for a wider range of commercial applications.

BRIEF DESCRIPTION OF DRAWINGS

The present disclosure will be understood more fully from the detailed description given below and from the accompanying drawings of various embodiments, which, however, should not be taken to limit the present disclosure to the specific embodiments, but are for explanation and understanding only.

DETAILED DESCRIPTION

Figure 1A:
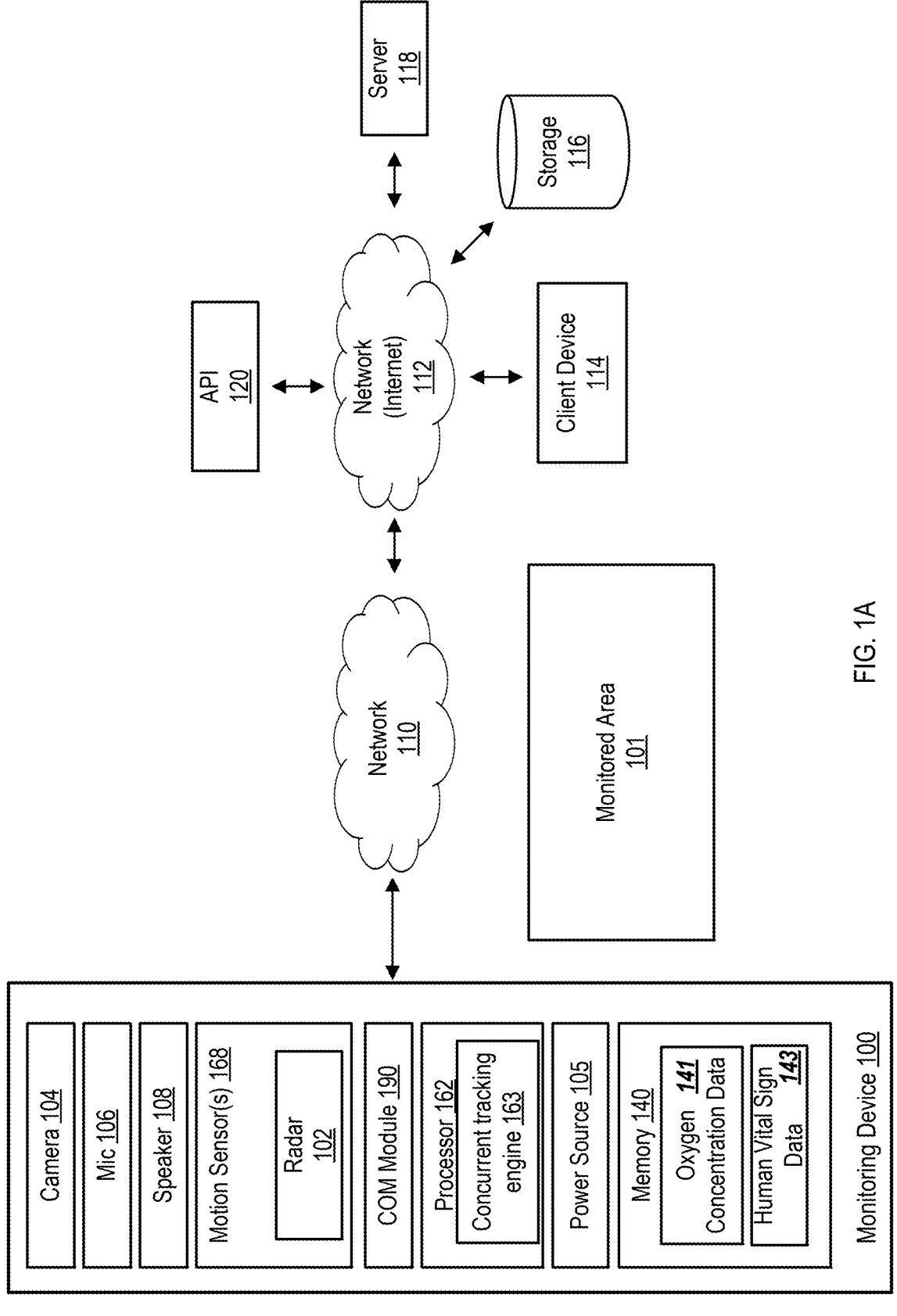
FIG. 1A illustrates an example environment including a monitoring device to monitor a human vital sign of a user and oxygen concentration levels according to at least one embodiment.

Technologies directed to are concurrent monitoring indoor oxygen-deficiency and human vital signs with mmWave radars described. The air' natural oxygen concentration level is around 21 percent, under normal atmospheric pressure conditions. However, natural oxygen in the air can be displaced by certain gases, including nitrogen and argon. Some of the causes that lead to oxygen deficiency are leaking natural gas lines, decomposing organic matter, such as animal, human, or plant waste, leading to the production of methane, carbon monoxide, carbon dioxide, and hydrogen sulfide that displace or consume oxygen. Even corrosion, such as rust, or fermentation, or other forms of oxidation will consume oxygen and pose a hazard. Indoor air pollution can be anywhere from 2 to over 100 times as high as outdoor pollution. Oxygen levels below the safe threshold of 19.5 percent can lead to health hazards such as asphyxiation. The risk is higher if the person is sleeping and unaware of the imminent hazard. For example, at 19 percent, a person can feel some adverse physiological effects, but they may not be noticeable. At 15-19 percent, a person at rest can have impaired thinking and attention, increased pulse and breathing rate, reduced coordination, decreased ability to work strenuously, and/or reduced physical and intellectual performance without awareness. At 12-15 percent, a person can have poor judgement, faulty coordination, abnormal fatigue upon exertion, and/or be emotionally upset. At 10-12 percent, a person can have very poor judgement and coordination, impaired respiration that may cause permanent heart damage, can faint within a few minutes without warning, and/or can experience nausea and vomiting. At less than 10 percent, a person can experience the inability to move, faint almost immediately, loss of consciousness, convulsions, and/or death. The effects of oxygen-deficient exposure can cause other health effects at the different oxygen concentration levels. The Occupational Safety and Health Administration (OHSA), in the Respiratory Protection Standard, 29 CFR 1910.134, has determined the optimal range of oxygen concentration levels in the air for humans to be between 19.5 and 23.5 percent.

Aspects of the present disclosure can concurrently monitor oxygen concentration levels and human vital signs using FMCW waveforms and a specific TDM chirp-frame structure of mmWave radars. The TDM chirp-frame structure can concurrently assess human vital signs and oxygen-deficiency in air, by leveraging oxygen absorption peaks in the 60 GHz mmWave band. Concurrent monitoring of oxygen-deficiency and vital signs could be leveraged to provide alerts and seek medical assistance as appropriate. Aspects of the present disclosure can be used in consumer and industrial applications. A chirp is a cycle of a radar cycle that changes in frequency throughout a period of time before repeating. A frame is a period of time during which a radar samples a monitored area 101 with a transmit signal, which includes a sequence of chirps, to capture a data set capable of being processed by one or more processing functions to perform object and motion detection. As such, each frame may include multiple chirps in order to capture sufficient data for object and motion detection processing. A chirp that is sent out reflects off surfaces and returns to the radar as reflection signals. Accordingly, the more chirps that are sent out per frame, the more data is available to be processed, and the more accurately objects may be detected.

FIG. 1A illustrates an example environment including a monitoring device 100 to monitor a human vital sign of a user and oxygen concentration levels according to at least one embodiment. The monitoring device 100 may include a camera 104, a power source 105, a microphone 106, a speaker 108, a memory 140, a processor 162, one or more motion sensors 168 (including a radar 102), and a communication module 190. The monitoring device 100 may be configured to monitor a monitored area 101. The processor 162 may include, and may also be referred to as, a controller or a microcontroller, and may include multiple processors in some embodiments. The processor 162 can concurrently monitor a human vital sign of a user in the monitored area 101 and an oxygen concentration level in the air in the monitored area 101 (i.e., the ambient environment of the monitoring device 100).

In an example mode of operation, the monitoring device 100 communicates with a wireless network 110 of a user. Although the wireless network 110 is referred to herein as "wireless," in some embodiments may not be wireless, such as where the monitoring device 100 is connected to the user's network via an Ethernet connection, for example. The wireless network 110 is connected to another network 112. The networks 110 and 112 may be the same network, in some of the present embodiments. The networks 110 and 112, may include but are not limited to the Internet, a Wi-Fi network compatible with the IEEE 802.11 standard and/or other wireless communication standard(s) including but not limited to WAP (Wireless Application Protocol), GPRS (General Packet Radio Service), GSM (Global System for Mobile Communication), LTE, VoLTE, LoRaWAN, LPWAN, RPMA, LTE Cat-"X" (e.g. LTE Cat 1, LTE Cat 0, LTE CatM1, LTE Cat NB1), CDMA (Code Division Multiple Access), TDMA (Time Division Multiple Access), FDMA (Frequency Division Multiple Access), and/or OFDMA (Orthogonal Frequency Division Multiple Access) cellular phone networks, GPS, CDPD (cellular digital packet data), Z-Wave, RIM (Research in Motion, Limited) duplex paging network, Bluetooth radio, an IEEE 802.11-based radio frequency network, or a combination thereof.

As described below, the monitoring device 100 may communicate with a client device 114 of the user via the wireless network 110 and/or the network 112. The client device 114 may include, for example, a computer, a laptop, a tablet, a mobile telephone (may also be referred to as a cellular telephone), such as a smartphone, a personal digital assistant (PDA), or another communication device capable of receiving and/or transmitting data across one or both of the networks 110, 112. The client device 114 may include a display (e.g., similar to the user interface (display) 1010 of FIG. 10, described below) and related components capable of displaying data associated with the monitoring device 100. The client device 114 may also include a speaker and related components capable of providing alerts to the user or another person responsible for the user, and may also include a microphone.

The monitoring device 100 may also communicate with one or more remote storage device(s) 116, one or more servers 118, and/or an application programming interface (API) 120 via the wireless network 110 and the network 112 (Internet/PSTN). While FIG. 1A illustrates the remote storage device 116, the server 118, and the API 120 as components separate from the network 112, it is to be understood that the remote storage device 116, the server 118, and/or the API 120 may be considered to be components of the network 112.

According to one or more aspects of the present embodiments, when a person arrives at the monitoring device 100, the monitoring device 100 detects the user's presence and begins capturing video images within a field of view of the camera 104 and/or using the motion sensors 168 to capture motion data. The field of view of the camera 104 may correspond to the monitored area 101. The monitoring device 100 may also capture audio through the microphone 106. The monitoring device 100 may detect the user's presence by detecting motion using the camera 104 and/or the motion sensor 168, and/or by detecting that the visitor has depressed a button on the monitoring device 100.

In response to the detection of certain conditions by the monitoring device 100, the monitoring device 100 sends an alert to the client device 114 via the wireless network 110 and/or the network 112. The monitoring device 100 may also send motion data and oxygen concentration levels, and may also send audio and video, to the client device 114 of the user (e.g., via the network 112 and/or the server 118). If an administrator answers the alert, two-way audio communication may then occur between the administrator and the user through the monitoring device 100 and the client device 114. The administrator may view the user throughout the duration of the call, but the user cannot see the administrator (unless the monitoring device 100 includes a display, which it may in some embodiments).

The motion data and oxygen concentration levels captured by the motion sensors 168 (and, in some embodiments, the video images captured by the camera 104 or the audio captured by the microphone 106) may be uploaded and recorded on the remote storage device 116. In some of the present embodiments, the motion data and oxygen concentration levels may be recorded on the remote storage device 116 even if the user (or administrator) chooses to ignore the alert sent to the user's client device 114. In such embodiments, the user (or administrator) may access the motion data and oxygen concentration levels at a later time by accessing the remote storage device 116 using the user's client device 114.

The API 120 may include, for example, a server (e.g., a bare-metal server, or a virtual machine, or a machine running in a backend infrastructure as a service), or multiple servers networked together, exposing at least one API to client(s) accessing it. These servers may include components such as application servers (e.g., software servers), depending upon what other components are included, such as a caching layer, or database layers, or other components. The API 120 may, for example, include many such applications, each of which communicate with one another using their public APIs. In some embodiments, the API 120 may hold the bulk of the user data and offer the user management capabilities, leaving the clients to have very limited state.

The API 120 is a set of routines, protocols, and tools for building software and applications. An API expresses a software component in terms of its operations, inputs, outputs, and underlying types, defining functionalities that are independent of their respective implementations, which allows definitions and implementations to vary without compromising the interface. Advantageously, an API may provide a programmer with access to an application's functionality without the programmer needing to modify the application itself, or even understand how the application works. An API may be for a web-based system, an operating system, or a database system, and it provides facilities to develop applications for that system using a given programming language. In addition to accessing databases or computer hardware like hard disk drives or video cards, an API can case the work of programming GUI components. For example, an API can facilitate integration of new features into existing applications (a so-called "plug-in API"). An API can also assist otherwise distinct applications with sharing data, which can help to integrate and enhance the functionalities of the applications.

In various embodiments, the API 120 includes one or more services (also referred to as network services). A network service is an application that provides data storage, manipulation, presentation, communication, and/or other capability. Network services are often implemented using a client-server architecture based on application-layer network protocols. Each service may be provided by a server component running on one or more computers (such as a dedicated server computer offering multiple services) and accessed via a network by client components running on other devices. However, the client and server components can both be run on the same machine. Clients and servers may have a user interface, and sometimes other hardware associated with them.

The memory 140 may be transitory and/or non-transitory and may represent one or both of volatile memory (e.g., SRAM, DRAM, computational RAM, other volatile memory, or any combination thereof) and non-volatile memory (e.g., FLASH, ROM, magnetic media, optical media, other non-volatile memory, or any combination thereof). Part or all of the memory 140 may be integrated with the processor 162. The memory 140 can store oxygen concentration data 141 and human vital sign data 143 measured in the monitored area 101. The memory 140 can store instructions corresponding to a concurrent tracking engine 163 that concurrently monitors human vital signs and oxygen concentration levels. The processor 162 can execute the instructions of the concurrent tracking engine 163 to perform the operations described herein. The instructions can be computer-executable instructions that, if executed, cause the processor 162 (or monitoring device) to perform operations as described herein.

Figure 1B:
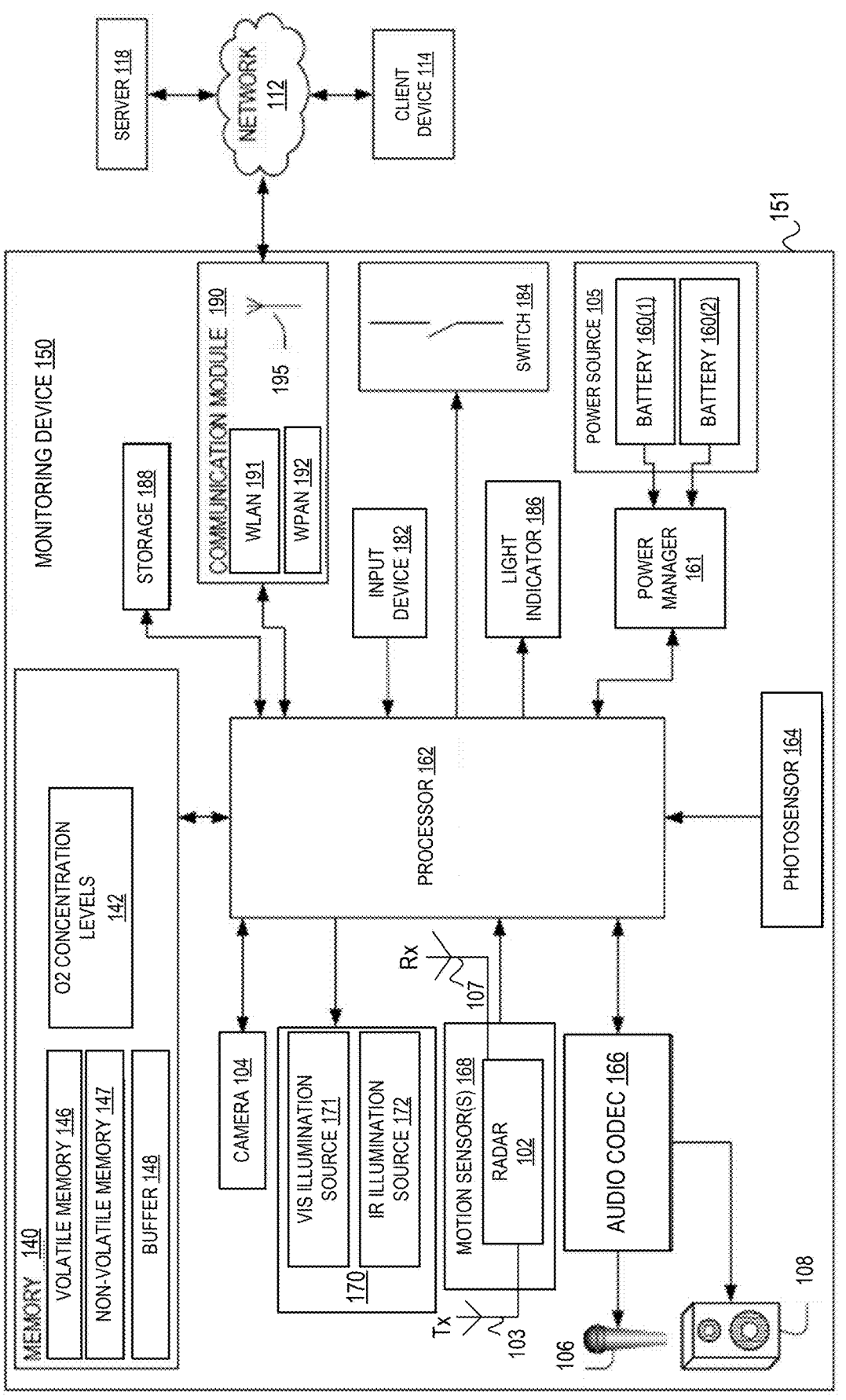
FIG. 1B illustrates a monitoring device in a network for monitoring human vital signs of a user and oxygen concentration levels according to at least one embodiment.

FIG. 1B illustrates a monitoring device 150 in a network for monitoring human vital signs of a user and oxygen concentration levels according to at least one embodiment.

The monitoring device 150 is similar to monitoring device 100 as noted by similar reference numbers. In various embodiments, the monitoring device 100 includes a power source 105, a memory 140, and a communication module 190. An embodiment of the monitoring device 150 may also include a housing 151 to encapsulate the majority of the illustrated components, a photosensor 164, an audio codec 166, an illumination source 170, an input device 182, a light indicator 186, each of which, when included, may be communicatively coupled to the processor 162, which will be discussed.

The monitoring device 150 may also include a power manager 161. The power source 105 includes at least two batteries 160(1) and 160(2), in some of the present embodiments. However, in other embodiments, the power source 105 may include more or fewer batteries, including zero batteries if the power source 105 is hardwired to an electrical power source. In alternative embodiments, the batteries 160(1) and 160(2) are fuel cells, solar arrays, or other low voltage power source. Each of the batteries 160(1) and 160(2) may be electrically connected to the power manager 161. The audio codec 166 may drive the speaker 108 and receive input from the microphone 106. The illumination source 170 may include a visible illumination source 171 and an infrared illumination source 172. The input device 182 may be, for example, a button, an electrical switch, and/or a manually operated electromechanical device.

The power manager 161 manages the power source 105 to provide electrical power to operate the monitoring device 150. The power manager 161 may include an electronic circuit that operates to condition power from the batteries 160 and to select which of the batteries 160(1) and 160(2) (in embodiments with more than one battery) power is drawn from. For example, the power manager 161 may draw power from the battery 160(1), and may switch to draw power from the battery 160(2) when the battery 160(1) is drained. By drawing power from only one of the batteries 160 at a time, the monitoring device 150 may continue operation when the depleted one of the batteries 160 is removed for recharging. In some embodiments, the monitoring device 150 may further include a switch 184 controlled by the processor 162 to activate the external illumination source 170.

The processor 162 may perform data processing and various other functions of the monitoring device 150, as described below. The memory 140 may include volatile memory 146 and non-volatile memory 147. In some embodiments, the processor 162, the volatile memory 146, the non-volatile memory 147, and/or programmable input/output peripherals (not shown) may be configured as an integrated circuit. The volatile memory 146 may be implemented as DDR3 or DDR4 SDRAM (double data rate type three or four synchronous dynamic random-access memory) or the like future generation memory. The non-volatile memory 147 may be implemented as NAND flash memory. The memory 140 may store instructions, that when executed by at least one processor such as the processor 162, cause the monitoring device to perform functions and operations of concurrent monitoring of oxygen concentration levels and human vital signs as described herein.

Although the volatile memory 146 and the non-volatile memory 147 are shown outside the box representing the processor 162 in the example of FIG. 1B, in some embodiments the volatile memory 146 and/or the non-volatile memory 147 may be physically incorporated with the processor 162, such as on the same integrated circuit (chip). The volatile memory 146 and/or the non-volatile memory 147, regardless of their physical location, may be shared by one or more other components (in addition to the processor 162) of the monitoring device 150. In certain embodiments, the monitoring device 150 includes additional storage 188 that may be implemented as any type of non-volatile data storage, such as, for example, and without limitation, hard disks/drives, flash memory, or any other suitable memory/ storage element. In some embodiments, the non-volatile memory 147 and the additional storage 188 may be combined as a single non-volatile memory. The additional storage 188, when included, may be operatively connected to the processor 162 and may be used to store oxygen concentration level data and vital sign data captured by the monitoring device 150, as described in further detail below.

In some embodiments, the camera 104 and the infrared illumination source 172 may cooperate to facilitate night vision functionality of the monitoring device 150. For example, the photosensor 164 may be configured to detect a level of ambient light about the monitoring device 150. The processor 162 may use the input from the photosensor 164 to control operation of the infrared illumination source 172 and the camera 104 to activate and deactivate night vision, as described in further detail below. In some embodiments, the camera 104 may include a video recording sensor or a camera chip. In some embodiments, the infrared illumination source 172 may include one or more IR light-emitting diodes (LEDs).

The transfer of digital audio between the user (via the user's client device 114) and a second user (e.g., an administrator) may be compressed and decompressed using the audio codec 166, as described below. The motion sensor 168 may include the radar 102 and optionally include one or more passive infrared (PIR) sensors or other type of sensor capable of detecting and communicating to the processor 162 the presence and/or motion of an object within its field of view. When triggered by the motion sensor 168, the processor 162 may perform one or more functions, as described below.

In various embodiments, the radar 102 is designed with different types of radar, including but not limited to, FMCW radar, pulse or pulse-Doppler radar, or a combination of one or more of these radar types. Thus, the radar 102 may be a frequency-modulated continuous wave radar or a pulse radar, or a combination of the two, as will be discussed in more detail. Different types of frequency modulated (FM) radar may be referred to jointly as FM radar. The monitoring device 150 may further include, or be coupled to, one or more radar antenna, including at least one transmit antenna 103, coupled to a transmitter (Tx), in order to transmit radar signals, and one or more receive antennas 107, coupled to a receiver (Rx), to receive reflected radar signals. In one embodiment, the transmitter and receiver are combined and are simply referred to as a receiver.

In various embodiments, the FMCW radar, also referred to as continuous-wave frequency-modulated (CWFM) radar, is a short-range measuring radar set capable of determining distance, but also adaptable to include Doppler and thus the ability to measure the speed of a moving object, which aids in identifying objects. The distance measurement along with the speed measurement increases reliability when there is more than one source of reflection arriving at the radar antenna. In FMCW radar, the transmitted signal of a known stable frequency continuous wave varies up and down in frequency over a fixed period of time by a modulating signal. Frequency difference between the receive signal and the transmit signal increases with delay, and hence with distance. This smears out, or blurs, the Doppler signal. Reflections (or echoes) received back from a target are then mixed with the transmitted signal to produce a beat signal, which will give the distance of the target after demodulation.

The modulations possible in FMCW vary, so long as frequency varies, including but not limited to sine wave (like an air raid siren), sawtooth wave (like a chirp from a bird), triangular wave (like a police siren in the United States), or a square wave (like a siren in the United Kingdom). Sawtooth modulation is the most used in FMCW radars where range is desired for objects that may lack rotating parts. Range information is mixed with the Doppler velocity using this technique. Modulation can be turned off during alternate scans to identify velocity using unmodulated carrier frequency shift. This allows range and velocity to be found with one radar set. Triangle wave modulation can be used to achieve the same goal. Sinusoidal FM may be used when both range and velocity are desired simultaneously for complex objects with multiple moving parts like turbine fan blades, helicopter blades (including as on a drone), or propellers. This processing reduces the effect of complex spectra modulation produced by rotating parts that introduce errors into the range measurement process. For simplicity of explanation, all of these waveform FM types will be referred to as "chirps," meaning a cycle of a radar signal that changes in frequency throughout a period of time before repeating.

In various embodiments, operational parameters of FMCW radar may be adjusted. These operational parameters include, but are not limited to, chirps per frame, frame per second (or frame rate), antenna configuration (e.g., number of active receive antennas being used), chirp duration, and the various digital signal processing (DSP) or central processing unit (CPU) functions employed to process received radar signals. In some embodiments, each radar 102 may include a digital signal processor and at least one CPU, e.g., a processing core, to perform these functions. In other embodiments, the digital signal processor is located off-package of the radar 102 and may be located elsewhere on the monitoring device 100, including possibly integrated within the processor 162. Regardless of where located, the radar 102 as is referenced herein is assumed to include the digital signal processor and at least one CPU core.

In the disclosed embodiments, as discussed, a frame may be understood to be a period of time during which the radar 102 samples the monitored area 101 to capture a data set capable of being processed by one or more processing functions to perform object detection and object monitoring. As such, each frame may include multiple chirps in order to capture sufficient data for object detection processing. The DSP/CPU functions include, but are not limited to, stationary object removal, range Fast Fourier Transform (FFT) processing, amplitude thresholding, angle of arrival estimation, and Doppler FFT processing.

An FFT is an algorithm that computes the discrete Fourier transform (DFT) of a sequence or its inverse (IDFT). Such Fourier analysis converts a signal from its original domain (such as time or space) to a presentation in the frequency domain and vice versa. An FFT reduces the number of computations needed for N points of the sequence from $2N^2$ to $2N*lg(N)$, where "lg" is the base-2 logarithm. The discrete Fourier transform can be computed using an FFT by means of the Danielson-Lanczos lemma if the number of points N is a power of two. If the number of points N is not a power of two, a transform can be performed on sets of points corresponding to the prime factors of N, which is slightly degraded in speed. An efficient real Fourier transform algorithm or a fast Hartley transform gives a further increase in speed by approximately a factor of two. Base-4 and base-8 FFTs use optimized code, and can be 20-30% faster than base-2 FFTs. Prime factorization is slow when the factors are large, but discrete Fourier transforms can be made fast for N=2, 3, 4, 5, 7, 8, 11, 13, and 16 using the Winograd transform algorithm.

Stationary object removal is a process of subtracting one frame (or a combination of previous frames) from the current frame to remove any unchanging signals from the data. An object that has not moved will be zeroed out by doing this. The goal is to only look at objects that are moving in space across time.

Range FFT is the process of running the intermediate frequency (IF, the mixture of the transmitted signal with the incoming reflected signal) through an FFT to convert the received frequencies into distances. Ultimately, the time-delay of each reflected signal is what translates into a frequency, and the FFT translates this into a superposition of distances. Each distance will have some amplitude associated with it depending on how strong the received signal was from that target.

Amplitude thresholding is the process of setting some threshold above the measured background noise, and seeing if the amplitudes of received signals exceed that threshold. If exceeding, then a detection is possible.

Angle of Arrival (AoA) estimation may involve the triangulation of reflected signals to determine an angle at which the reflected signals are arriving. When multiple receive antennas 307 are enabled, it is possible to compare the phase data from each receiver coupled to the respective receive antenna. Depending on spatial separation of these receive antennas (distance and plane of separation), the radar 102 may locate not only the distance of the targets, but also the angle from which the reflection arrived at the radar 102. This allows localization of an object in two-dimensional (2D) or three-dimensional (3D) space rather than just a single dimensional distance.

With reference to Doppler FFT, when multiple chirps are enabled, the radar 102 may perform a second FFT on received frames of data to not only resolve the distances of objects (from the first FFT), but also the speed at which the objects are moving (from the second FFT). This is more accurate than deducing the speed of objects by measuring distance/time throughout multiple frames. Use of the Doppler FFT may enable determining an identity of a detected object, such as resolving that the object detected is a human, not a cat or a leaf.

The memory 140 may further include an oxygen concentration levels information 142, a buffer 148, and, in certain embodiments, may also include the volatile memory 146 and/or the non-volatile memory 147. The oxygen concentration levels information 142 may be stored in a data structure such as a table, matrix, spreadsheet, or the like. In at least one embodiment, the oxygen concentration levels information 142 can be stored in a lookup table (LUT) keyed to RSSI values corresponding to different oxygen concentration percentages. The buffer 148 may be part of the volatile memory 146 and/or the non-volatile memory 147. The buffer 148 may be a rolling buffer such as a circular buffer, a circular queue, a cyclic buffer, or a ring buffer, or other data structure that uses a single, fixed-size buffer as if it were connected end-to-end. Data from the radar 102 may be stored in the buffer 148 in response to certain triggers or conditions.

In some embodiments, the processor 162 monitors, based on processing of received radar signals, a human vital sign of a user and measures a RSSI value at 60 GHz, and the processor may look up the oxygen concentration percentage corresponding to the RSSI value at 60 GHz to determine an oxygen concentration level of the air.

The communication module 190 includes at least one antenna 195, and is configured to handle communication between the monitoring device 150 and other, external devices or receivers, and to route incoming/outgoing data appropriately. For example, inbound data from the antenna 195 may be routed through the communication module 190 before being directed to the processor 162, and outbound data from the processor 162 may be routed through the communication module 190 before being directed to the antenna 195. The communication module 190 may include one or more transceiver modules capable of transmitting and receiving data, and using, for example, one or more protocols and/or technologies, such as a Wi-Fi network compatible with the IEEE 802.11 standard and/or other wireless communication standard(s) including but not limited to WAP (Wireless Application Protocol), GPRS (General Packet Radio Service), GSM (Global System for Mobile Communication), LTE, VoLTE, LoRaWAN, LPWAN, RPMA, LTE Cat-"X" (e.g. LTE Cat 1, LTE Cat 0, LTE CatM1, LTE Cat NB1), CDMA (Code Division Multiple Access), TDMA (Time Division Multiple Access), FDMA (Frequency Division Multiple Access), and/or OFDMA (Orthogonal Frequency Division Multiple Access) cellular phone networks, GPS, CDPD (cellular digital packet data), Z-Wave, RIM (Research in Motion, Limited) duplex paging network, Bluetooth radio, or an IEEE 802.11-based radio frequency network or any other protocol and/or technology. In the illustrated embodiment, the communication module 190 may include a wireless local area network (WLAN) chip 191 (e.g., chip with the Wi-Fi® technology) and a wireless personal area network (WPAN) chip 192 (e.g., chip with the Bluetooth® technology) that implement medium-range wireless communication protocols and short-range wireless communication protocols, respectively, but these components are merely examples and are not limiting. Further, while the WLAN chip 191 and the WPAN chip 192 are illustrated within the box representing the communication module 190, the embodiment illustrated in FIG. 1B is merely an example, and in some embodiments the WLAN chip 191 and/or the WPAN chip 192 may not necessarily be physically incorporated with the communication module 190.

In some embodiments, the communication module 190 may further include a wireless repeater (not shown, may also be referred to as a wireless range extender). The wireless repeater may be configured to receive a wireless signal from a wireless router (or another network device) in the user's wireless network 110 and rebroadcast the signal. Wireless devices that are not within the broadcast range of the wireless router, or that only weakly receive the wireless signal from the wireless router, may receive the rebroadcast signal from the wireless repeater of the communication module 190, and may thus connect to the user's wireless network 110 through the monitoring device 150. In some embodiments, the wireless repeater may include one or more transceiver modules (not shown) capable of transmitting and receiving data, and using, for example, one or more medium-range wireless communication protocols and/or technologies, such as Wi-Fi (IEEE 802.11), long-range wireless communication protocols, such as WiMAX (IEEE 802.16), or any other protocol and/or technology.

When a user in the monitored area 101 speaks, audio from the user can be captured by the microphone 106 and may be compressed by the audio codec 166. Digital audio data may then be sent through the communication module 190 to the network 112 (in some embodiments via the user's wireless network 110 of FIG. 1A), routed by the server 118 and/or the API 120, and delivered to the user's client device 114. When the user speaks, the user's client device 114 may capture digital audio data, which may then be transferred through the network 112 and/or the user's wireless network 110, the communication module 190, and the processor 162 to the audio codec 166 where it is decoded and emitted to the visitor through the speaker 108, which may be driven by an audio driver.

The input device 182 may have one or more functions, such as changing an operating mode of the monitoring device 150 and/or triggering a reset of the monitoring device 150. For example, when the input device 182 is activated (e.g., pressed and released), it may cause the communication module 190 of the monitoring device 150 to enter an access point (AP) mode, which may facilitate connecting the monitoring device 150 to the user's wireless network 110 and/or the network 112. Alternatively, or in addition, when the input device 182 is activated (e.g., pressed and held) for at least a threshold amount of time, it may trigger the erasing of any data stored by the volatile memory 146 and/or by the non-volatile memory 147, and/or may trigger a reboot of the processor 162.

In certain embodiments, the monitoring device 150 may be configured to recognize a "wake-up" word or phrase (e.g., using the microphone 106 and the processor 162) that triggers a command input mode. When the command input mode is triggered, the monitoring device 150 detects, using the microphone 106, a verbal command that may be recognized to cause the monitoring device 150 to perform an action. For example, in an embodiment, when the user, within the monitored area 101, says the wake-up word or phrase followed by "turn on the lights," the monitoring device 150 activates the illumination source 170. Similarly, in another embodiment, when the user, within the monitored area 101, says the wake-up word or phrase followed by "turn off the lights," the monitoring device 150 deactivates the illumination source 170. In certain embodiments, recognition of the wake-up word or phrase may only occur when the motion sensor 168 and/or the camera 104 detects motion within the monitored area 101. In some embodiments, the available commands may be preconfigured within the monitoring device 150. In other embodiments, the recognizable commands may be learned by the monitoring device 150 from the user. In some embodiments, the monitoring device 150 may be trained to recognize the voice of the user, and thereafter respond only to commands when that voice is recognized.

In certain embodiments, the monitoring device 150 may use the camera 104 to recognize a face (e.g., the face of an authorized user). For example, in an embodiment, the monitoring device 150 may include a learn mode through which the face(s) of one or more authorized user(s) is/are learned and stored within the non-volatile memory 147. Upon detecting and recognizing an authorized user's face, the monitoring device 150 may enter a command input mode, in another embodiment, whereby verbal commands from the authorized user are interpreted and executed by the monitoring device 150. In one example, where the authorized user stands facing the monitoring device 150 and says "turn the lights on," the security device of certain embodiments activates the illumination source 370 after recognizing the authorized user's face. Similarly, when the authorized user faces the monitoring device 150 and says "turn off the lights," the monitoring device 150 may deactivate the illumination source 170 after recognizing the authorized user's face. In some embodiments, the monitoring device 150 uses a lip-reading algorithm to interpret the authorized user's verbal command. In some embodiments, the monitoring device 150 detects gesture(s) by the authorized user, interpret the gesture as a command, and then executes that command. For example, where the authorized user faces the monitoring device 150 and makes an arm waving gesture, once the monitoring device 150 recognizes the face of the authorized user, the monitoring device 150 of this example detects the arm waving movements and activates the illumination source 370.

In certain embodiments, the radar 102 is able to distinguish different types of objects within the monitored area 101, where functionality of the monitoring device 150 may vary depending upon the type of object detected within the monitored area 101. For example, in an embodiment, the illumination source 170 may be activated when a vehicle and/or a person is detected, whereas data may start being captured only when a person is detected. As discussed, the radar 102 may use Doppler FFT processing to determine whether or not the detected object is a human.

In some embodiments, the radar 102 is a stand-alone device with integrated digital signal processing and other processing capabilities to perform the processing functions disclosed herein. In other words, the radar 102 is not integrated within the monitoring device 150. The stand-alone device may be a motion sensor that may function within a larger alarm system, for example. In one embodiment, the radar 102 is fitted within a housing, includes a power source, such as a battery, and is networked to a hub or base station of a home automation system, and optionally also to the client device 114.

Figure 2:
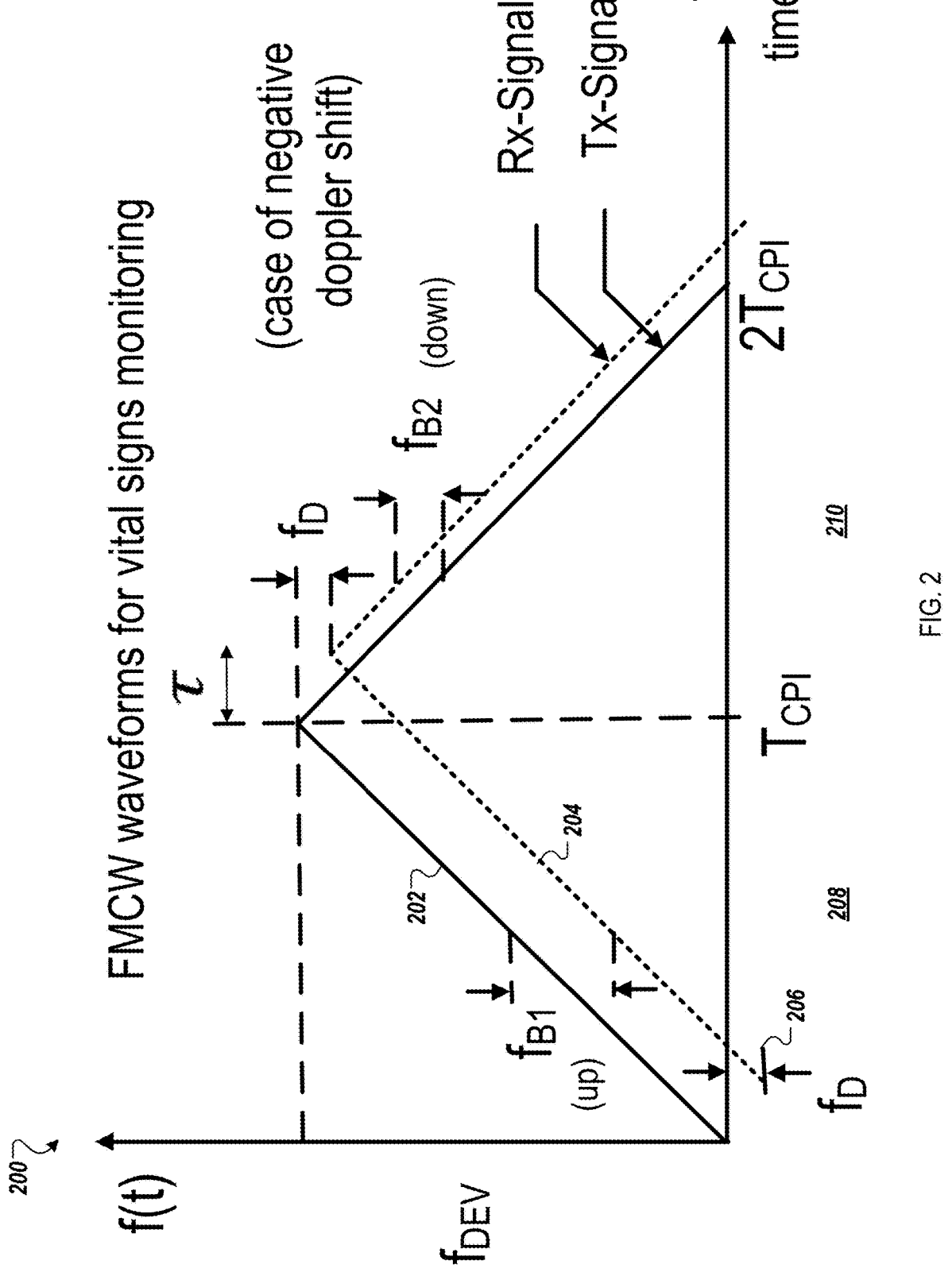
FIG. 2 illustrates frequency-modulated continuous wave (FMCW) waveforms for vital signs monitoring according to at least one embodiment.

FIG. 2 illustrates FMCW waveforms 200 for vital signs monitoring according to at least one embodiment. The FMCW waveforms 200 include a transmitted signal 202 of a known stable frequency continuous wave that varies up and down in frequency over a fixed period of time 201 (e.g., $2T_{CPI}$) by a modulating signal. The FMCW waveforms 200 include a received signal 204. The frequency difference 206 ($f_D$) between the received signal 204 and the transmitted signal 202 increases with delay, and hence with distance. This smears out, or blurs, the Doppler signal. Reflections (or echoes) received back from a target are then mixed with the transmitted signal 202 to produce a beat signal (302 in FIG. 3), which gives the distance of the target after demodulation. While uses of the term vary in the art, "chirps" herein refer to a cycle of a radar signal that changes in frequency throughout a period of time before repeating.

As illustrated in FIG. 2, the transmitted signal 202 is a single triangular-type chirp that increases in frequency for a first period 208 (e.g., $T_{CPI}$) and decreases in frequency for a second period 210 (e.g., $T_{CPI}$). The first period 208 is a first amount of time and the second period 210 is a second amount of time that follows the first amount of time consecutively. The first amount of time and the second amount of time are equal to the fixed period of time 201 (e.g., $2T_{CPI}$). Unlike a single ramp or a sawtooth chirp type, a single triangular chirp of the transmitted signal 202 can be used to estimate both range and radial velocity. Thus, it is possible to track time evolution of phase accurately. This in turn can be used to estimate both amplitude and periodicity of motion of a user and vibrations for vital sign monitoring, such as vibrations caused by breathing and heart beats. The human vital sign being monitored can include breathing rates of a user, heart rates of a user, or both. Alternatively, other human vital signs can be measured by the monitoring device using the radar and/or one or more additional types of sensors. By adjusting the shape of the triangular chirp, finer resolutions in phase can be achieved with a single triangular chirp. This in turn can reproduce breathing (and heart rate) waveforms as good as respiration belts used in polysomnography, gold standard (PGG) in sleep medicine/ studies. This accuracy is vital to detect sleep disorders like sleep apnea.

From FIG. 2, both range and radial velocity can be calculated using the equations (1A) and (1B):

$$f_{B1} = \frac{2f_{dev}}{cT_{CPI}}R - \frac{2}{\lambda}V_r \qquad (1A)$$

$$f_{B2} = -\frac{2f_{dev}}{cT_{CPI}}R - \frac{2}{\lambda}V_r \qquad (1B)$$

Figure 3:
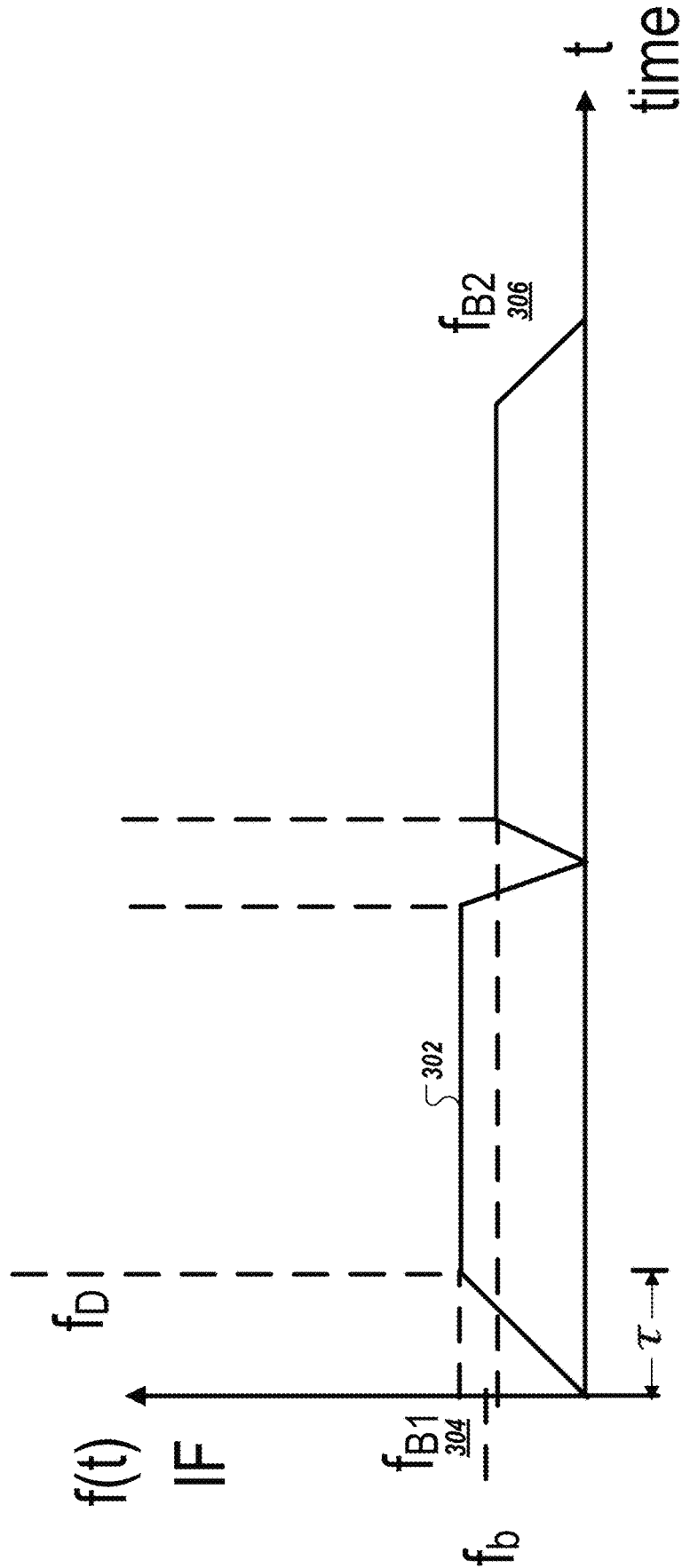
FIG. 3 is a graph of an intermediate signal with a first portion corresponding to an up-chirp of the FMCW waveforms of FIG. 2 and a second portion corresponding to a down-chirp of the FMCW waveforms of FIG. 2, according to at least one embodiment.

FIG. 3 is a graph of an intermediate signal 302 with a first portion corresponding to an up-chirp of the FMCW waveforms of FIG. 2 and a second portion corresponding to a down-chirp of the FMCW waveforms of FIG. 2, according to at least one embodiment. As described above, reflections (or echoes) received back from a target are then mixed with the transmitted signal 202 to produce the intermediate signal 302. The intermediate signal 302 can be a beat signal with a first beat frequency 304 ($f_{B1}$) detected from a first portion of the FMCW waveforms and a second beat frequency 306 ($f_{B2}$) from a second portion of the FMCW waveforms. Range FFTs can be computed from equations (1A) and (1B) above to produce peaks corresponding to phase information (e.g., different phases).

Figure 4:
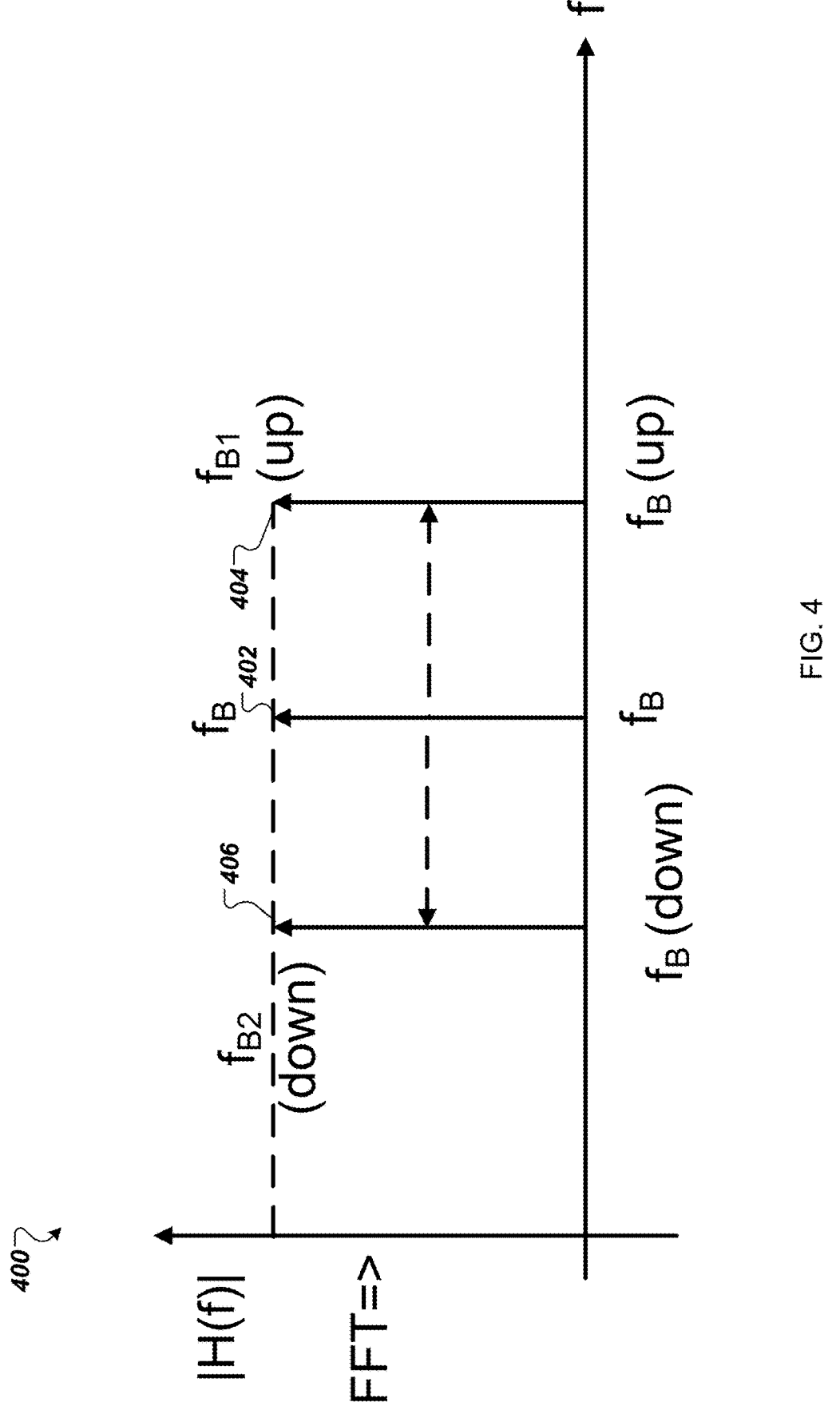
FIG. 4 is a graph of a Fast Fourier Transform (FFT) of the intermediate signal of FIG. 3, according to at least one embodiment.

FIG. 4 is a graph 400 of an FFT of the intermediate signal of FIG. 3, according to at least one embodiment. The graph 400 shows a first peak 402 corresponding to a beat frequency, a second peak 404 corresponding to an up-chirp, and a third peak 406 corresponding to a down-chirp of the single triangular-type chirp. The peaks correspond to phase information (e.g., different phases). The phase estimates can be determined using equation (2) as follows:

$$\Delta\phi = \frac{4\pi V_r T_{CPI}}{\lambda}, \text{ where } T_c = 2T_{CPI} \qquad (2)$$
$$= \frac{8\pi V_r T_{CPI}}{\lambda}$$

The displacement or vibration caused by a breathing motion can be estimated using equation (3) or (4) as follows:

$$\Delta\phi = \frac{4\pi\Delta d}{\lambda}, \qquad (3)$$

$$\text{Or } \Delta d = \frac{\lambda d\phi}{4\pi} \qquad (4)$$

Figures 5A, 5B:
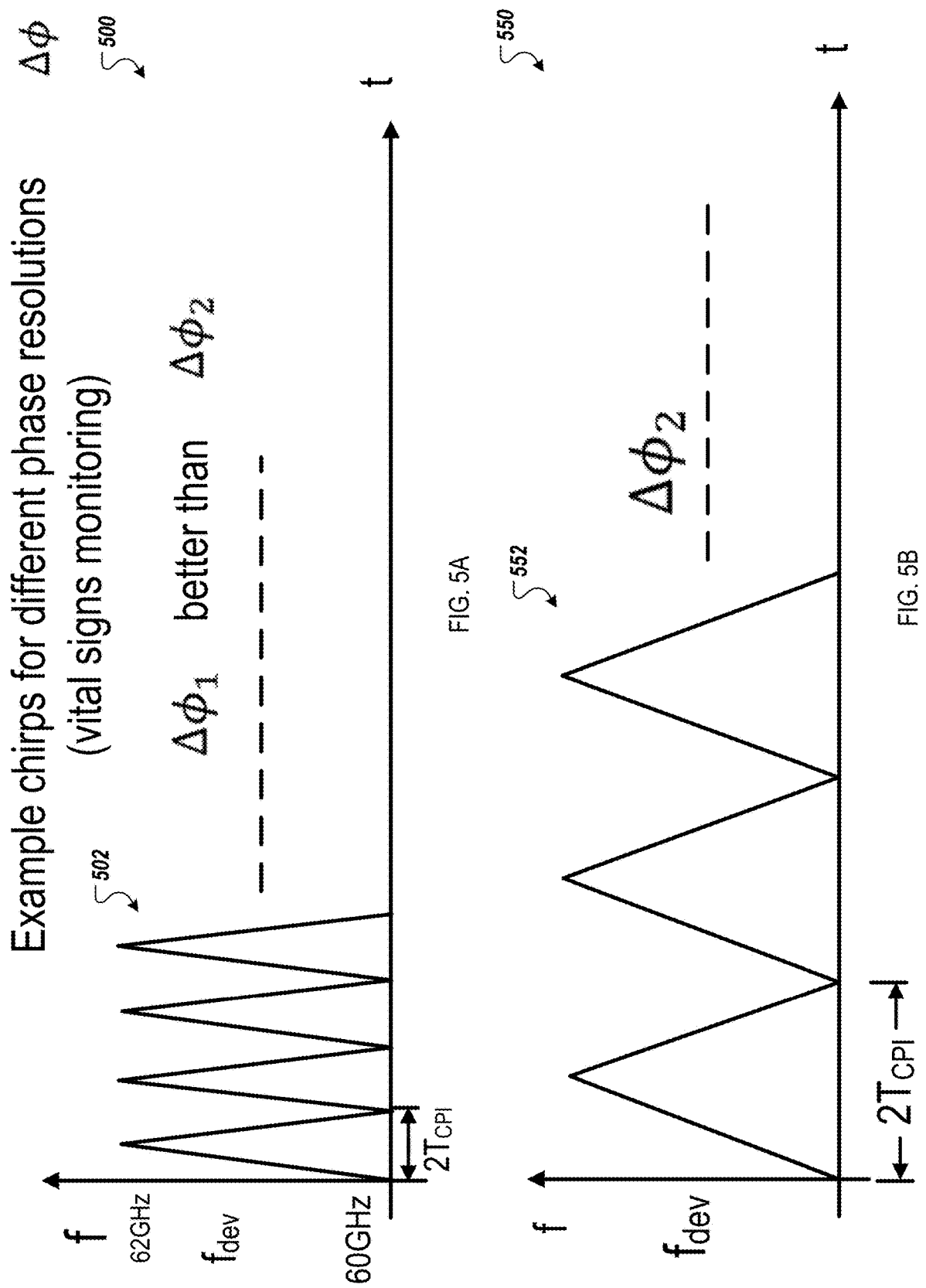
FIG. 5A is a graph illustrating a first set of chirps with a triangular-type chirp and a first phase resolution for vital sign monitoring according to at least one embodiment.
FIG. 5B is a graph illustrating a second set of chirps with a triangular-type chirp and a second phase resolution for vital sign monitoring according to at least one embodiment.

Different slopes of the triangular-type chirp can be used for different phase resolutions for vital sign monitoring, such as illustrated in the examples of FIGS. 5A-5B.

FIG. 5A is a graph 500 illustrating a first set of chirps 502 with a triangular-type chirp and a first phase resolution for vital sign monitoring according to at least one embodiment. FIG. 5B is a graph 550 illustrating a second set of chirps 552 with a triangular-type chirp and a second phase resolution for vital sign monitoring according to at least one embodiment. As illustrated in FIGS. 5A-5B, the first phase resolution can achieve better accuracy of the phase information than the second phase resolution.

Figures 6A, 6B:
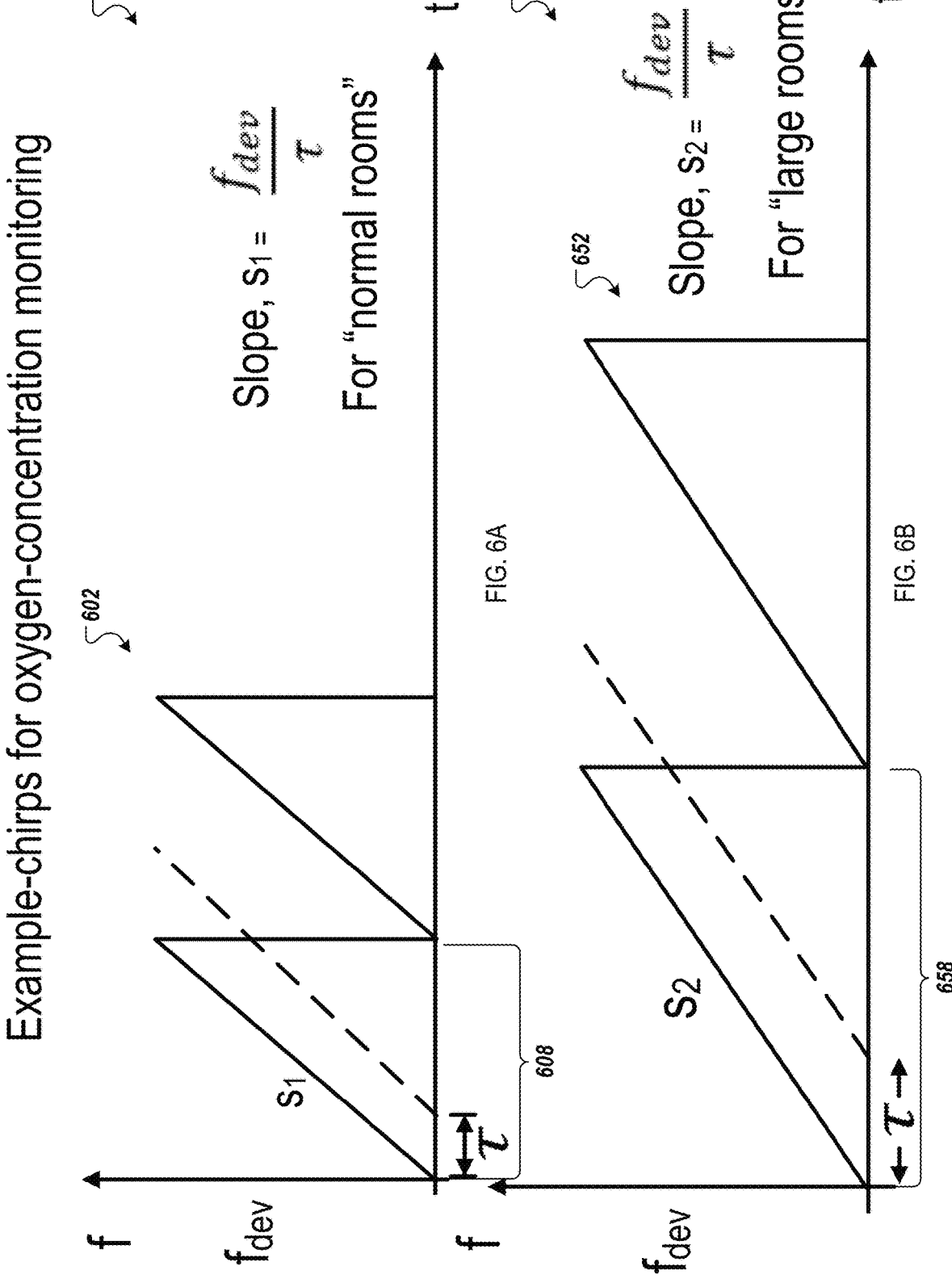
FIG. 6A is a graph illustrating a first set of chirps with a ramp-type chirp and a first slope for oxygen concentration level monitoring according to at least one embodiment.
FIG. 6B is a graph illustrating a second set of chirps with a ramp-type chirp with a second slope for oxygen concentration level monitoring according to at least one embodiment.

FIG. 6A is a graph 600 illustrating a first set of chirps 602 with a ramp-type chirp and a first slope for oxygen concentration level monitoring according to at least one embodiment. Unlike the single triangular-type chirp of FIGS. 5A-5B, the ramp-type chirp only increases in frequency for a third period 608 (e.g., $T_{CPI}$). The third period 608 can be a third amount of time that is half the fixed period of time 201 (e.g., $2T_{CPI}$). The ramp-type chirp can increase to a higher frequency than the triangular-type chirp. The slope of the first set of chirps 602 can be expressed in equation (5) as follows:

$$\text{Slope}, s_i = \frac{f_B}{\tau} \qquad (5)$$

FIG. 6B is a graph 650 illustrating a second set of chirps 652 with a ramp-type chirp with a second slope for oxygen concentration level monitoring according to at least one embodiment. A chirp of the second set of chirps 652 increases in frequency for a third period 658 (e.g., $T_{CPI}$). The third period 658 is a third amount of time that is greater than the third period 608 of the first set of chirps 602. A chirp of the first set of chirps 602 has a first slope and a chirp of the second set of chirps 652 has a second slope that is less than the first slope. The second set of chirps, with the lower slope, can be used for larger rooms.

In at least one embodiment, the triangular-type chirps of FIGS. 5A-5B and the ramp types of FIGS. 6A-6B can be combined into a single TDM chirp-frame structure for concurrent monitoring of indoor/outdoor air quality (e.g., oxygen concentration percentage) and human vital signs with mmWave sensors, as described below with respect to FIGS. 7A-7C.

Figure 7A:
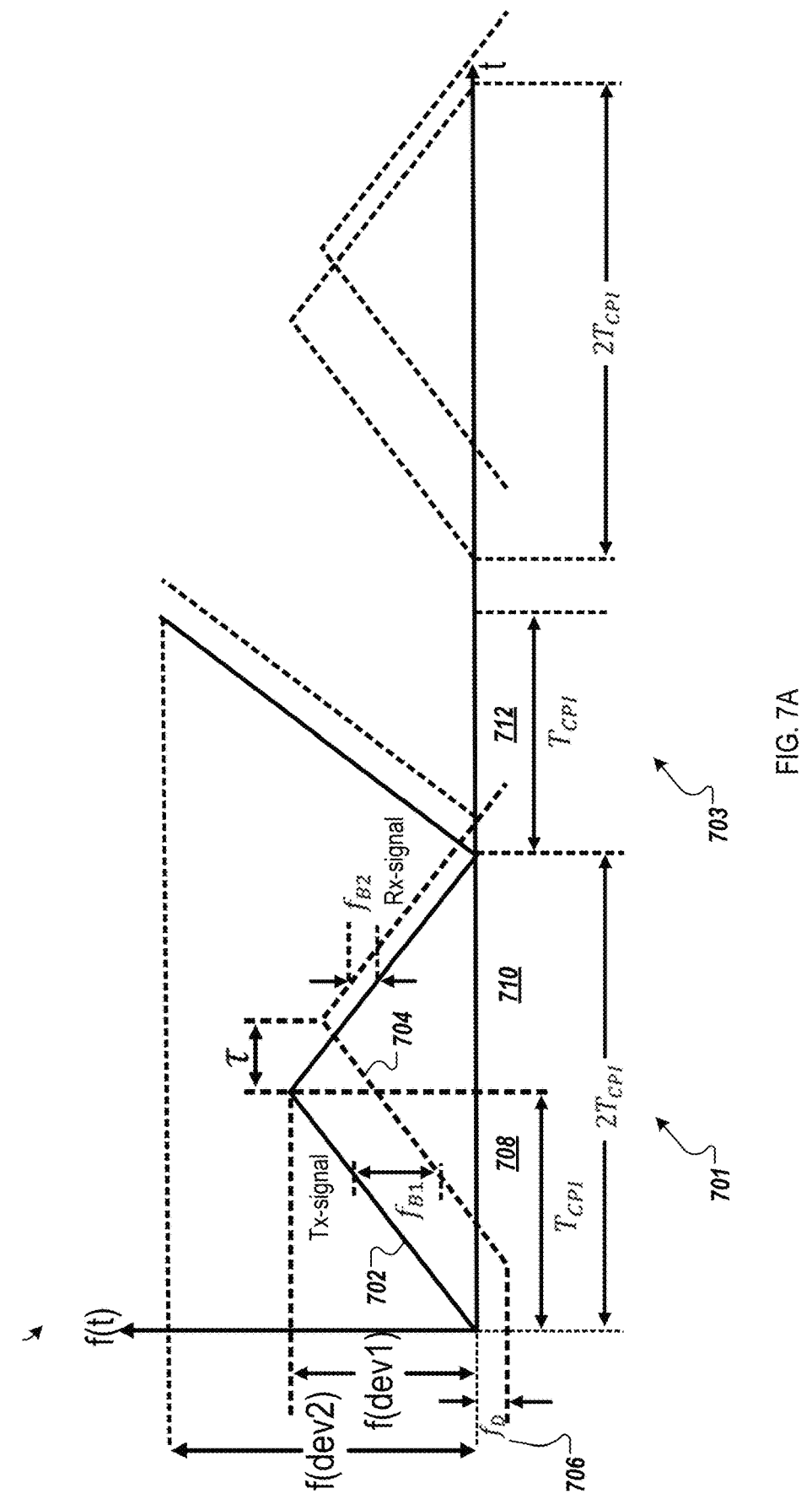
FIG. 7A illustrates FMCW waveforms for concurrent monitoring of oxygen concentration levels in air and human vital signs according to at least one embodiment.

FIG. 7A illustrates FMCW waveforms 700 for concurrent monitoring of oxygen concentration levels in air and human vital signs according to at least one embodiment. The FMCW waveforms 700 include a transmitted signal 702 of a known stable frequency continuous wave that varies up and down in frequency over a first fixed period of time 701 (e.g., $2T_{CPI}$) by a modulating signal and varies up in frequency over a second fixed period of time 703 (e.g., $T_{CPI}$). The FMCW waveforms 700 include a received signal 704. The frequency difference 606 ($f_D$) between the received signal 704 and the transmitted signal 702 increases with delay, and hence with distance. This smears out, or blurs, the Doppler signal. Reflections (or echoes) received back from a target are then mixed with the transmitted signal 702 to produce a beat signal, which gives the distance of the target after demodulation.

Figure 7B:
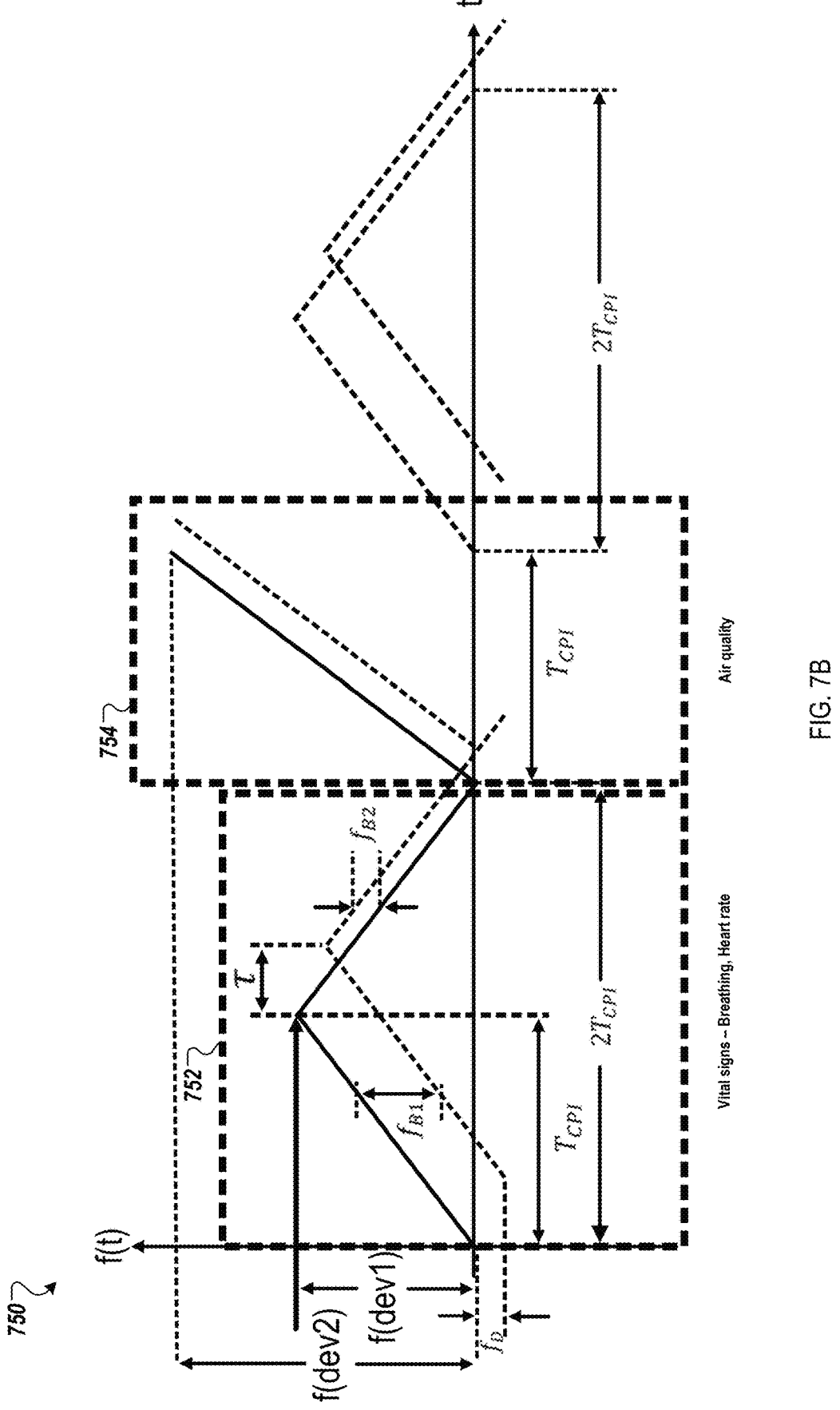
FIG. 7B illustrates a TDM chirp-frame structure having a first portion for vital signs monitoring and a second portion for oxygen concentration level monitoring according to at least one embodiment.

As illustrated in FIG. 7, the transmitted signal 702 has a single triangular-type chirp that increases in frequency for a first period 708 (e.g., $T_{CPI}$) and decreases in frequency for a second period 710 (e.g., $T_{CPI}$) and a single ramp-type chirp that increases in frequency for a third period 712 (e.g., $T_{CPI}$). The first period 708 is a first amount of time and the second period 710 is a second amount of time that follows the first amount of time consecutively. The third period 712 is a third amount of time that follows the second amount of time consecutively. The first amount of time and the second amount of time are equal to the first fixed period of time 701 (e.g., $2T_{CPI}$) and the third amount of time is equal to the second fixed period of time 703. The single triangular chirp of the transmitted signal 702 can be used to estimate both range and radial velocity and the single ramp chirp of the transmitted signal 704 can be used to determine an oxygen concentration level. Thus, it is possible to track time evolution of phase accurately. This in turn can be used to estimate both amplitude and periodicity of motion of a user and vibrations for vital sign monitoring, such as vibrations caused by breathing and heart beats. The human vital sign being monitored can include breathing rates of a user, heart rates of a user, or both. The ramp chirp in the transmitted signal 702 can concurrently measure a value corresponding to an oxygen concentration level. By adjusting the shape of the triangular chirp, finer resolutions in phase can be achieved with a single triangular chirp. This in turn can reproduce breathing (and heart rate) waveforms as good as respiration belts used in polysomnography, gold standard (PGG) in sleep medicine/studies. This accuracy is vital to detect sleep disorders like sleep apnea. By adjusting the slope of the ramp chirp, the oxygen concentration percentages can be measured for different sizes of rooms. The transmitted signal 702 and the received signal 704 can be part of a TDM chirp-frame structure that can concurrently assess human vital signs and oxygen-deficiency in air, by leveraging oxygen absorption peaks in the 60 GHz mmWave band. Concurrent monitoring of oxygen-deficiency and vital signs could be leveraged to provide alerts and seek medical assistance as described herein. An example of the TDM chirp-frame structure is illustrated in FIG. 7B.

FIG. 7B illustrates a TDM chirp-frame structure 750 having a first portion for vital signs monitoring and a second portion for oxygen concentration level monitoring according to at least one embodiment. The TDM chirp-frame structure 750 include a first chirp 752 and a second chirp 754. The first chirp 752 is a triangular chirp and the second chirp 754 is a ramp chirp. The first chirp 752 results in a first portion of the received signal being used for monitoring vital signs and the second chirp 756 results in a second portion of the received signal being used for monitoring air quality. As illustrated in FIG. 7B, the TDM chirp-frame structure 750 can be repeated.

In another embodiment, the TDM chirp-frame structure can include one or more triangular chirps followed by one or more ramp chirps. For example, the sequence of chirps in the TDM chirp-frame structure can include multiple triangular chirps followed by one or more ramp chirps.

As described herein, the oxygen absorption peaks in the 60 GHz mm Wave band can be leveraged for air quality monitoring. To establish oxygen percentage correlations with RSSI values, a cavity-enhanced mmWave spectroscopy method can be used to create a lookup table (LUT) that correlates RSSI values and oxygen concentration percentages. The LUT can store variations in the absorption peak levels at 60 GHz resonance corresponding to oxygen concentration percentages. The frequency sweep in the ramp chirp (e.g., 55 GHz to 65 GHZ) can be used to measure a range of a stationary object (e.g., wall) within a specific room size and the measured RSSI values at 60 GHz due to path loss (two-way) would be stable and indicate the absorption peak levels (or resonance) corresponding to the oxygen concentration levels within the room, such as illustrated in FIG. 7C.

Figure 7C:
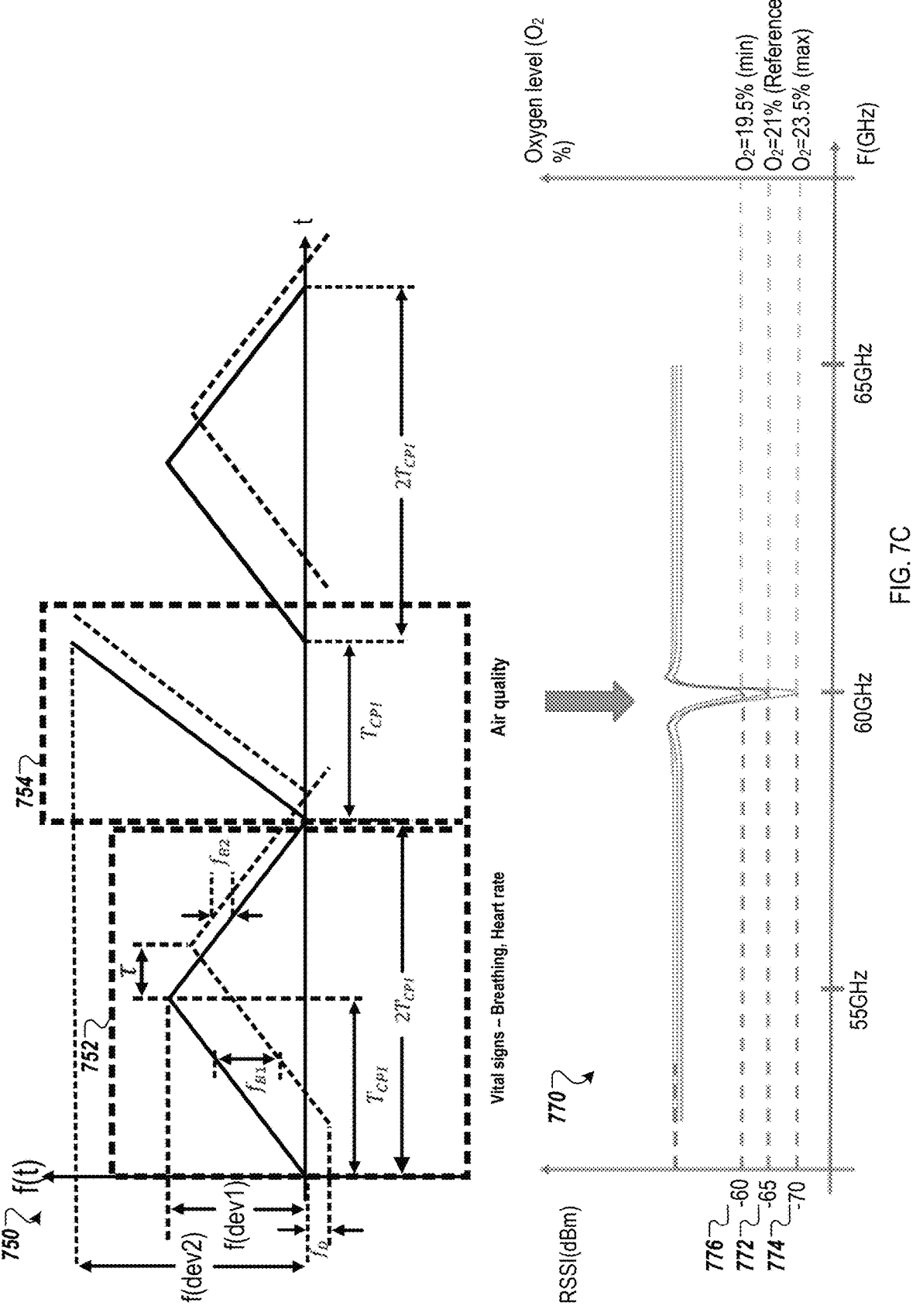
FIG. 7C illustrates a graph of received signal strength indicator (RSSI) values corresponding to oxygen concentration percentages at 60 GHz for oxygen concentration level monitoring according to at least one embodiment.

FIG. 7C illustrates a graph 770 of RSSI values corresponding to oxygen concentration percentages at 60 GHz for oxygen concentration level monitoring according to at least one embodiment. The graph 770 include a first RSSI value 772 (e.g., −65 dB) at 60 GHz that corresponds to a first oxygen concentration percentage (e.g., 21% reference). The graph 770 include a second RSSI value 774 (e.g., −70 dB)

at 60 GHz that corresponds to a second oxygen concentration percentage (e.g., 23.5% maximum). The graph 770 include a third RSSI value 776 (e.g., −60 dB) at 60 GHz that corresponds to a third oxygen concentration percentage (e.g., 19.5% minimum). The RSSI values at 60 GHz can be measured in the received signal corresponding to the ramp chirp (754) of the TDM chirp-frame structure 750 (reproduced in FIG. 7C).

Figure 8:
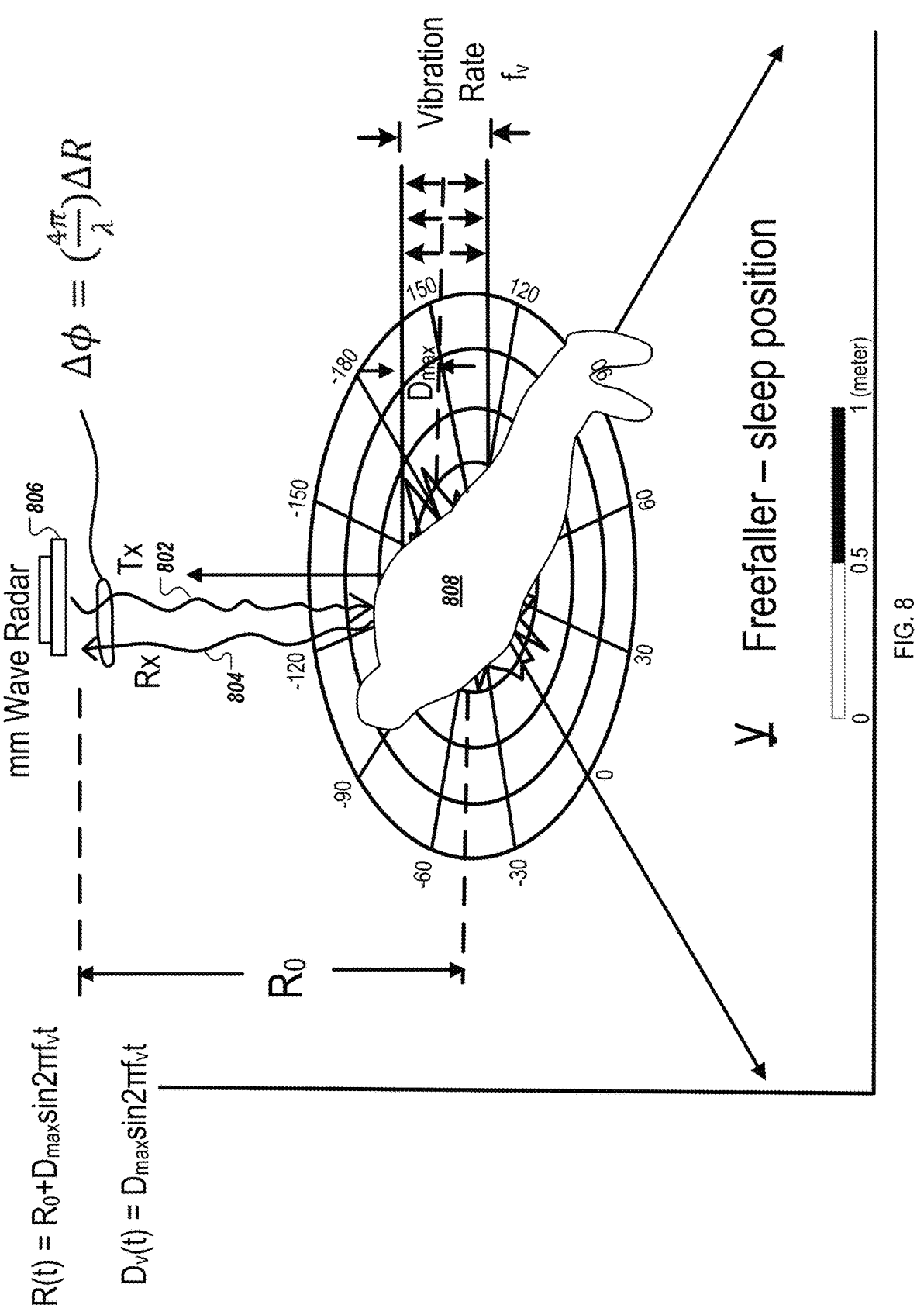
FIG. 8 illustrates a transmit signal and a receive signal from a mmWave radar for monitoring human vital signs of a user in a sleep position according to at least one embodiment.

FIG. 8 illustrates a transmit signal 802 and a receive signal 804 from a mmWave radar 806 for monitoring human vital signs of a user 808 in a sleep position according to at least one embodiment. The transmit signal 802 and receive signal 804 can be used to determine a range ($R_0$) and a displacement caused by vibrations from breathing, a heart beat, or both. The receive signal 804 is an echo signal from the target, user 808, and can be expressed in equation (6) below:

$$S_r(t) = A_R e^{j\left[2\pi f_0 t + \frac{4\pi R(t)}{\lambda}\right]} \tag{6}$$

where $A_R$ is the amplitude, $f_0$ is the frequency of the transmit signal 802, and $\lambda$ is the wavelength. The phase is expressed in equation (7) below:

$$, \phi[t] = \frac{4\pi}{\lambda}R(t) = \frac{4\pi}{\lambda}R_0 + \frac{4\pi}{\lambda}D_{max}\ \sin(2\pi f_v t) \tag{7}$$

By substituting equation (7) into equation (6), the echo signal can be represented in equation (8) below:

$$S_R(t) = A_R e^{\left[j\frac{4\pi}{\lambda}R_0\right]} e^{\left[j2\pi f_0 t + \frac{4\pi}{\lambda}D_{max}\sin\ 2\pi f_v t\right]} \tag{8}$$

The phase modulation is expressed in equation (9) below:

$$\theta(t) = \frac{4\pi}{\lambda}D_v(t) = \frac{4\pi}{\lambda}D_{max}\sin\ 2\pi f_v t \tag{9}$$

Thus, the received signal 804 (Rx-echo signal) is expressed in equation (10) below:

$$S_R(t) = A_R e^{\left(j\frac{4\pi}{\lambda}R_0\right)} e^{\left(j2\pi f_0 t + \theta(t)\right)} \tag{10}$$

Vibrations caused by breathing induce micro-Doppler shift and is given by the time-derivative of phase modulation, $\theta(t)$, as expressed in equation (11) below:

$$f_{microD}(t) = \frac{1}{2\pi}\frac{d}{dt}\theta(t) = \frac{4\pi}{\lambda}f_v D_{max}\cos\ 2\pi f_v t \tag{11}$$

The radial velocity (or Los velocity) is expressed in equation (12) below:

$$v = \frac{\lambda}{2}f_{microD}(t) = 2\pi f_v D_{max}\cos\ 2\pi f_v t \tag{12}$$

As illustrated in FIG. 8, the range between the mmWave radar 806 and the user 808 can be expressed in equation (13), the displacement caused by vibration can be expressed in equation (14), and the difference in phase, ΔΦ, is expressed in equation (15) below:

$$R(t) = R_0 + D_{max} \sin 2\mu f_v t \qquad (13)$$

$$D_v(t) = D_{max} \sin 2\mu f_v t \qquad (14)$$

$$\Delta\phi = \left(\frac{4\pi}{\lambda}\right)\Delta R \qquad (15)$$

Figure 9:
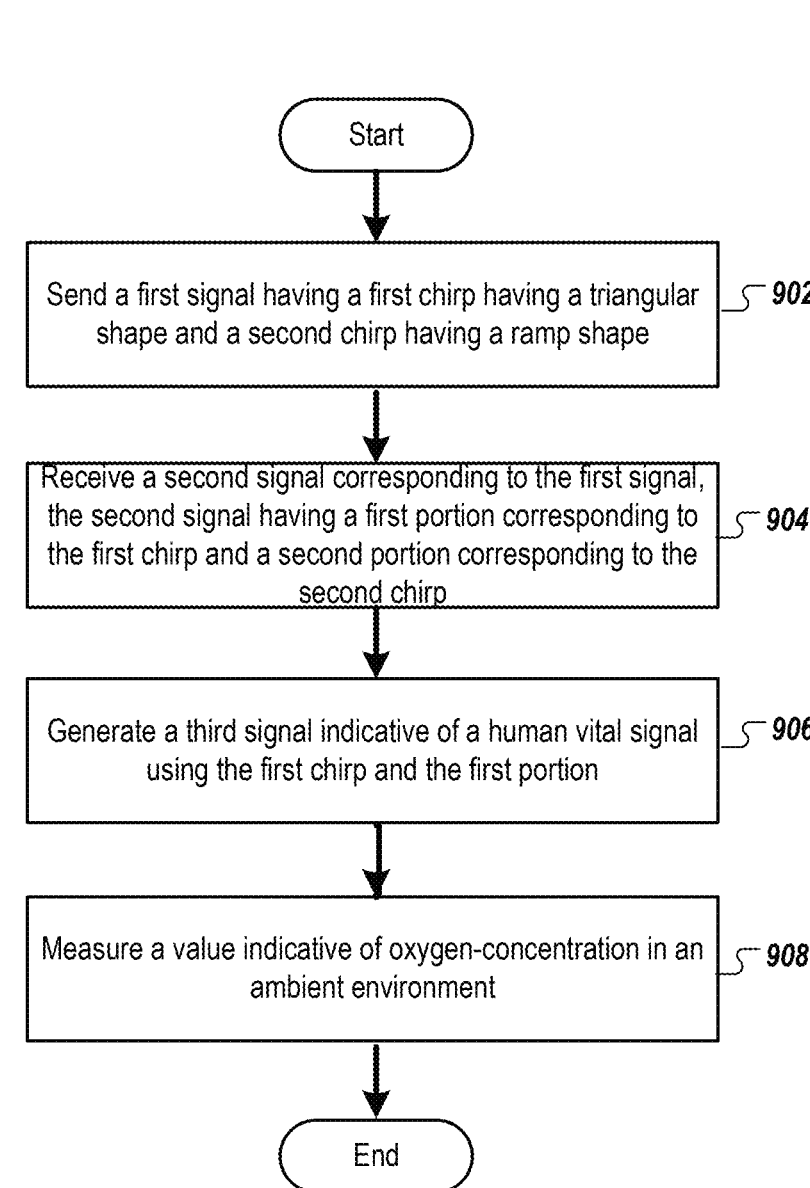
FIG. 9 is a flow diagram of a method for concurrent monitoring of a human vital sign and oxygen concentration levels according to at least one embodiment.

FIG. 9 is a flow diagram of a method 900 for concurrent monitoring of a human vital sign and oxygen concentration levels according to at least one embodiment. The method 900 may be performed by processing logic that may include hardware (circuitry, dedicated logic, etc.), software (such as is run on a general purpose computer system or a dedicated machine), firmware, or some combination thereof. For example, the method 900 may be performed by the monitoring device 100 or 150, and particularly by the processor 162 executing instructions stored in the memory 140 for performance of aspects of the method 900.

The method 900 begins by the processing logic sending a first signal having a first chirp having a triangular shape and a second chirp having a ramp shape (block 902). The frequency of the first signal is in the mmWave frequency range. The processing logic receives a second signal corresponding to the first signal (block 904). The second signal comprising a first portion corresponding to the first chirp and a second portion corresponding to the second chirp. The processing logic generates a third signal indicative of a human vital sign of a user using the first chirp and the first portion (block 906). The human vital sign can be a heartbeat signal (or heart rate of the user). The human vital sign can be a respiratory signal (or respiratory rate of the user). The processing logic measures, using the second chirp and the second portion, a value indicative of oxygen-concentration in an ambient environment of the device (block 908), and the method 900 ends. It should be noted that oxygen-concentration in the ambient environment can be defined as an oxygen concentration level or percentage.

In a further embodiment, the value is measured at block 908 by determining a RSSI value of the second portion at approximately 60 GHz and retrieving, from stored data, the value using the RSSI value. In at least one embodiment, the value can be associated with the RSSI value in a LUT. In another embodiment, the processing logic determines the value using the RSSI value in other manners.

In at least one embodiment, the processing logic sends, by the FMCW radar, a fourth signal having a sequence of chirps including a third chirp that is a triangular-type chirp that increases in frequency for a fourth period and decreases in frequency for a fifth period and a fourth chirp that is a ramp-type chirp that increases in frequency for a sixth period. In this embodiment, the fourth period is different than the first period. This can be a different phase resolution, as described above with respect to FIGS. 5A-5B. The processing logic receives by the FMCW radar, a fifth signal corresponding to the fourth signal. The fifth signal includes a first portion corresponding to the third chirp and a second portion corresponding to the fourth chirp. The processing logic generates, using the third chirp and the third portion, a sixth signal indicative of the human vital sign. The processing logic measures a second RSSI value of the second portion at approximately 60 GHz. The processing logic determines, using the second RSSI value, a second value indicative of oxygen-concentration in the ambient environment of the monitoring device.

In a further embodiment, the processing logic sends by the FMCW radar, a fourth signal having a sequence of chirps including a third chirp that is a triangular-type chirp that increases in frequency for a fourth period and decreases in frequency for a fifth period and a fourth chirp that is a ramp-type chirp that increases in frequency for a sixth period. In this embodiment, the fourth chirp increases in frequency to a frequency higher than the second chirp. This can be done for a larger room, for example. The processing logic receives, by the FMCW radar, a fifth signal corresponding to the fourth signal. The fifth signal includes a third portion corresponding to the third chirp and a fourth portion corresponding to the fourth chirp. The processing logic generates, using the third chirp and the third chirp portion, a sixth signal indicative of the human vital sign. The processing logic measures a second RSSI value of the second portion at approximately 60 GHz. The processing logic determines, using the second RSSI value, a second value indicative of oxygen-concentration in the ambient environment of the monitoring device.

In a further embodiment, the processing logic determines that the value is less than a first threshold value corresponding to a first percentage of oxygen concentration in the ambient environment (e.g., 19.5%) and provides an alert to the user in response to the value being less than the threshold value.

In another embodiment, the processing logic determines a RSSI value of the second portion at approximately 60 GHz and determines that the RSSI value is less than a RSSI threshold value associated with a first percentage of oxygen concentration in the ambient environment (e.g., 19.5%). In one embodiment, the RSSI threshold value can be set to an oxygen concentration level at which a user can experience changes in health or body conditions. In another embodiment, the RSSI threshold value can be set to an oxygen concentration level before a user experiences changes in healthy or body conditions. In another embodiment, the processing logic determines the value and the value is an RSSI value of the second portion at approximately 60 GHz. The processing logic determines that the RSSI value is less than a RSSI threshold value associated with a first percentage of the oxygen concentration in the ambient environment.

In another embodiment, the processing logic determines a first RSSI value of the second portion at approximately 60 GHz and determines that the RSSI value is less than a first RSSI threshold value associated with a first percentage of oxygen concentration in the ambient environment. The processing logic can provide a first alert to the user. The processing logic sends a fourth signal having a third chirp having the triangular shape and a fourth chirp having the ramp shape. The fourth signal is also in the mmWave frequency range. The processing logic receives a fifth signal corresponding to the fourth signal, the fifth signal comprising a third portion corresponding to the third chirp and a fourth portion corresponding to the fourth chirp. The processing logic determines a second RSSI value of the fourth portion at approximately 60 GHz and determines that the second RSSI value is less than a second RSSI threshold value associated with a second percentage of oxygen concentration in the ambient environment. The second RSSI threshold value is less than the first RSSI threshold value. The processing logic provides a second alert to the user. The second alert and the first alert are different types. For example, the first alert can be a first audible noise (e.g., a beep) to the user and the second alert can be a second audible noise (e.g., a siren), louder than the first audible noise. For another example, the first alert can be a first message and the second alert can be a second message being sent to a user device, such as an administrator that is monitoring the user.

In another embodiment, the processing logic generate the third signal at block 906 by estimating a range and a radial velocity of the user from the first portion. The processing logic generates phase estimates using the range and radial velocity and generates amplitudes estimates using the range and radial velocity. The processing logic generates the third signal using the phase estimates and the amplitude estimates.

In one embodiment, the first chirp increases in frequency for a first amount of time and decreases for a second amount of time and the second chirp increases in frequency for a third amount of time. In another embodiment, the triangular shape increase in frequency from a first time to a second time and decreases in frequency from the second time to a third time. The second chirp increases in frequency from the third time to a fourth time. In another embodiment, the first chirp has a first duration that is twice a second duration of the second chirp. In another embodiment, the first chirp increases in frequency from a first frequency to a second frequency and decreases from the second frequency to the first frequency, and the ramp shape increases in frequency from the first frequency to a third frequency greater than the second frequency. In another embodiment, the first chirp has a first peak frequency and the second chirp has a second peak frequency, the second peak frequency being greater than the first peak frequency.

In another embodiment, the processing logic sends, by an FMCW radar, a first signal having a TDM frame with a sequence of chirps having a first chirp having a triangular shape that increases in frequency for a first period and decreases in frequency for a second period and a second chirp having a ramp shape that increases in frequency for a third period. The processing logic receives, by the FMCW radar, a second signal corresponding to the first signal. The second signal comprising a first portion corresponding to the first chirp and a second portion corresponding to the second chirp. The processing logic generates a third signal indicative of a human vital sign of a user using the first chirp and the first portion. The human vital sign is a heart rate or a respiratory rate. The processing logic measures a RSSI value of the second portion at approximately 60 GHz and determines, using the RSSI value, a value indicative of oxygen-concentration in an ambient environment of the monitoring device. In at least one embodiment, the processing logic determines the value by retrieving, from stored data, the value using the RSSI value.

In at least one embodiment, the processing logic generates the third signal by estimating a range and a radial velocity of the user from the first portion. The processing logic generates phase estimates and amplitude estimates using the range and radial velocity. The processing logic generates the third signal using the phase estimates and the amplitude estimates.

Figure 10:
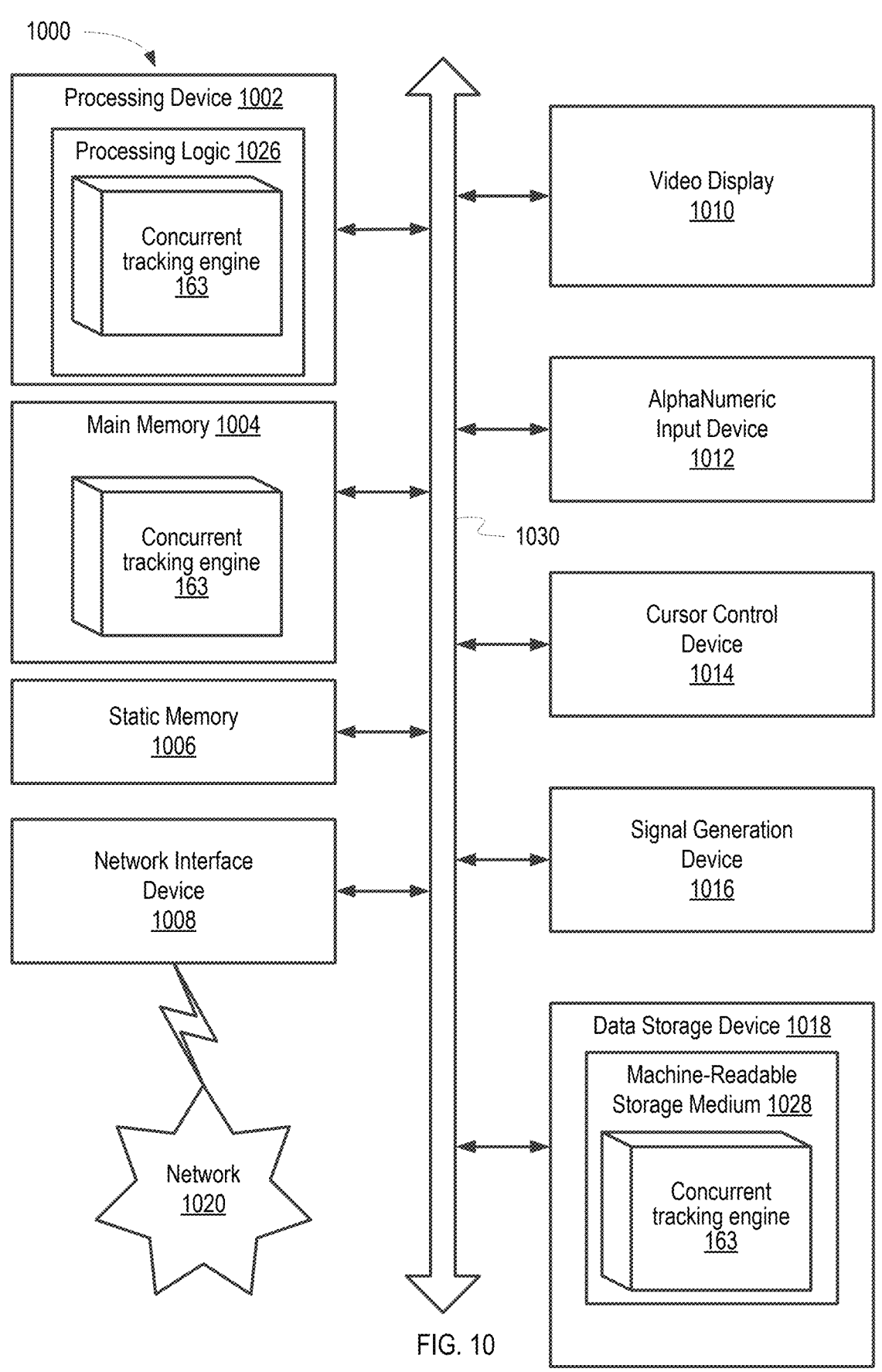
FIG. 10 is a diagrammatic representation of a machine in the example form of a computer system including a set of instructions executable by a computer to concurrently monitor oxygen concentration levels and human vital signs according to any one or more of the methodologies discussed herein.

FIG. 10 is a diagrammatic representation of a machine in the example form of a computer system 1000 including a set of instructions executable by a computer to concurrently monitor oxygen concentration levels and human vital signs according to any one or more of the methodologies discussed herein. In one embodiment, the computer may include instructions to enable execution of the processes and corresponding components shown and described in connection with FIGS. 1-9.

In alternative embodiments, the machine may be connected (e.g., networked) to other machines in a LAN, an intranet, an extranet, or the Internet. The machine may operate in the capacity of a server machine in a client-server network environment. The machine may be a personal computer (PC), a set-top box (STB), a server, a network router, switch or bridge, or any machine capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein The example computer system 1000 includes a processing device (processor) 1002, a main memory 1004 (e.g., read-only memory (ROM), flash memory, dynamic random access memory (DRAM) such as synchronous DRAM (SDRAM)), a static memory 1006 (e.g., flash memory, static random access memory (SRAM)), and a data storage device 1018, which communicate with each other via a bus 1030.

Processing device 1002 represents one or more general-purpose processing devices such as a microprocessor, central processing unit, or the like. More particularly, the processing device 1002 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1002 may also be one or more special-purpose processing devices such as an application specific integrated circuit (ASIC), a field programmable gate array (FPGA), a digital signal processor (DSP), network processor, or the like. In various implementations of the present disclosure, the processing device 1002 is configured to execute instructions for the concurrent tracking engine 163 that concurrently monitors human vital signs and oxygen concentration levels as set forth in the operations and processes described herein.

The computer system 1000 may further include a network interface device 1008. The computer system 1000 also may include a video display unit 1010 (e.g., a liquid crystal display (LCD) or a cathode ray tube (CRT)), an alphanumeric input device 1012 (e.g., a keyboard), a cursor control device 1014 (e.g., a mouse), and a signal generation device 1016 (e.g., a speaker).

The data storage device 1018 may include a computer-readable storage medium 1028 (or machine-readable medium) on which is stored one or more sets of instructions of the concurrent tracking engine 163 embodying any one or more of the methodologies or functions described herein. The instructions may also reside, completely or at least partially, within the main memory 1004 and/or within processing logic 1026 of the processing device 1002 during execution thereof by the computer system 1000, the main memory 1004 and the processing device 1002 also constituting computer-readable media.

The instructions may further be transmitted or received over a network 1020 via the network interface device 1008. While the computer-readable storage medium 1028 is shown in an example embodiment to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium that is capable of storing, encoding or carrying a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

The preceding description sets forth numerous specific details such as examples of specific systems, components, methods, and so forth, in order to provide a good understanding of several embodiments of the present disclosure. It will be apparent to one skilled in the art, however, that at least some embodiments of the present disclosure may be practiced without these specific details. In other instances, well-known components or methods are not described in detail or are presented in simple block diagram format in order to avoid unnecessarily obscuring the present disclosure. Thus, the specific details set forth are merely presented as examples. Particular implementations may vary from these example details and still be contemplated to be within the scope of the present disclosure. In the above description, numerous details are set forth.

It will be apparent, however, to one of ordinary skill in the art having the benefit of this disclosure, that embodiments of the disclosure may be practiced without these specific details. In some instances, well-known structures and devices are shown in block diagram form, rather than in detail, in order to avoid obscuring the description.

Some portions of the detailed description are presented in terms of algorithms and symbolic representations of operations on data bits within a computer memory. These algorithmic descriptions and representations are the means used by those skilled in the data processing arts to most effectively convey the substance of their work to others skilled in the art.

An algorithm is here, and generally, conceived to be a self-consistent sequence of steps leading to the desired result. The steps are those requiring physical manipulations of physical quantities. Usually, though not necessarily, these quantities take the form of electrical, magnetic, or optical signals capable of being stored, transferred, combined, compared, and otherwise manipulated. It has proven convenient at times, principally for reasons of common usage, to refer to these signals as bits, values, elements, symbols, characters, terms, numbers, or the like.

It should be borne in mind, however, that all of these and similar terms are to be associated with the appropriate physical quantities and are merely convenient labels applied to these quantities. Unless specifically stated otherwise as apparent from the above discussion, it is appreciated that throughout the description, discussions utilizing terms such as: detecting", "identifying", "determining", or the like, refer to the actions and processes of a computer system, or similar electronic computing device, that manipulates and transforms data represented as physical (e.g., electronic) quantities within the computer system's registers and memories into other data similarly represented as physical quantities within the computer system memories or registers or other such information storage, transmission or display devices.

Embodiments of the disclosure also relate to an apparatus for performing the operations herein. This apparatus may be specially constructed for the required purposes, or it may comprise a general purpose computer selectively activated or reconfigured by a computer program stored in the computer. Such a computer program may be stored in a computer-readable storage medium, such as, but not limited to, any type of disk including floppy disks, optical disks, CD-ROMs, and magnetic-optical disks, read-only memories (ROMs), random access memories (RAMs), EPROMS, EEPROMs, magnetic or optical cards, or any type of media suitable for storing electronic instructions.

The algorithms and displays presented herein are not inherently related to any particular computer or other apparatus. Various general-purpose systems may be used with programs in accordance with the teachings herein, or it may prove convenient to construct a more specialized apparatus to perform the required method steps. The required structure for a variety of these systems will appear from the description below. In addition, the present embodiments are not described with reference to any particular programming language. It will be appreciated that a variety of programming languages may be used to implement the teachings of the present disclosure as described herein. It should also be noted that the terms "when" or the phrase "in response to," as used herein, should be understood to indicate that there may be intervening time, intervening events, or both before the identified operation is performed.

It is to be understood that the above description is intended to be illustrative, and not restrictive. Many other embodiments will be apparent to those of skill in the art upon reading and understanding the above description. The scope of the disclosure should, therefore, be determined with reference to the appended claims, along with the full scope of equivalents to which such claims are entitled.

What is claimed is:

1. A monitoring device comprising:
   a frequency-modulated continuous wave (FMCW) radar that operates in a millimeter wave (mmWave) frequency range;
   a processing device coupled to the FMCW radar; and
   a memory coupled to the processing device to store computer-executable instructions that, if executed, cause the monitoring device to perform operations comprising:
   sending, by the FMCW radar, a first signal having a sequence of chirps comprising a first chirp that is a triangular-type chirp that increases in frequency for a first period and decreases in the frequency for a second period and a second chirp that is a ramp-type chirp that increases in the frequency for a third period;
   receiving, by the FMCW radar, a second signal corresponding to the first signal, the second signal comprising a first portion corresponding to the first chirp and a second portion corresponding to the second chirp;
   generating, by the processing device and using the first chirp and the first portion, a third signal indicative of a human vital sign, wherein the human vital sign is a heart rate or a respiratory rate;
   measuring, by the processing device, a received signal strength indicator (RSSI) value of the second portion at the frequency in a range of 55-65 GHz; and
   determining, by the processing device and using the RSSI value, a value indicative of oxygen-concentration in an ambient environment of the monitoring device.

2. The monitoring device of claim 1, wherein the operations further comprise:
   sending, by the FMCW radar, a fourth signal having the sequence of chirps comprising a third chirp that is the triangular-type chirp that increases in the frequency for a fourth period and decreases in the frequency for a fifth period and a fourth chirp that is the ramp-type chirp that increases in the frequency for a sixth period, wherein the fourth period is different than the first period;

receiving, by the FMCW radar, a fifth signal corresponding to the fourth signal, the fifth signal comprising a third portion corresponding to the third chirp and a fourth portion corresponding to the fourth chirp;

generating, by the processing device and using the third chirp and the third portion, a sixth signal indicative of the human vital sign;

measuring, by the processing device, a second RSSI value of the second portion at the frequency in the range of 55-65 GHz; and determining, by the processing device and using the second RSSI value, a second value indicative of the oxygen-concentration in the ambient environment of the monitoring device.

3. The monitoring device of claim 1, wherein the operations further comprise:

sending, by the FMCW radar, a fourth signal having the sequence of chirps comprising a third chirp that is the triangular-type chirp that increases in the frequency for a fourth period and decreases in the frequency for a fifth period and a fourth chirp that is the ramp-type chirp that increases in the frequency for a sixth period, wherein the fourth chirp increases in the frequency to a frequency higher than the second chirp;

receiving, by the FMCW radar, a fifth signal corresponding to the fourth signal, the fifth signal comprising a third portion corresponding to the third chirp and a fourth portion corresponding to the fourth chirp;

generating, by the processing device and using the third chirp and the third portion, a sixth signal indicative of the human vital sign;

measuring, by the processing device, a second RSSI value of the second portion at the frequency in the range of 55-65 GHz; and determining, by the processing device and using the second RSSI value, a second value indicative of the oxygen-concentration in the ambient environment of the monitoring device.

4. The monitoring device of claim 1, wherein the operations further comprise:

determining that the value is less than a first threshold value corresponding to a first percentage of the oxygen-concentration in the ambient environment; and providing an alert.

5. The monitoring device of claim 1, wherein the operations further comprise:

determining that the RSSI value is less than a RSSI threshold value associated with a first percentage of the oxygen-concentration in the ambient environment; and providing an alert.

6. The monitoring device of claim 1, wherein the operations further comprise:

determining that the RSSI value is less than a first RSSI threshold value associated with a first percentage of the oxygen-concentration;

providing a first alert;

sending a fourth signal having a third chirp having the triangular-type shape and a fourth chirp having the ramp-type chirp, wherein the fourth signal is in the millimeter wave (mmWave) frequency range;

receiving a fifth signal corresponding to the fourth signal, the fifth signal comprising a third portion corresponding to the third chirp and a fourth portion corresponding to the fourth chirp;

determining a second RSSI value of the fourth portion at the frequency in the range of 55-65 GHz;

determining that the second RSSI value is less than a second RSSI threshold value associated with a second percentage of the oxygen-concentration, wherein the second RSSI threshold value is less than the first RSSI threshold value; and providing a second alert, wherein the second alert and the first alert are of different types.

7. The monitoring device of claim 1, wherein the first chirp has a first duration that is twice a second duration of the second chirp.

8. A method of operating a device, the method comprising:

sending, by a frequency-modulated continuous wave (FMCW) radar that operates in a millimeter wave (mmWave) frequency range, a first signal having a sequence of chirps comprising a first chirp that is a triangular-type chirp that increases in frequency for a first period and decreases in the frequency for a second period and a second chirp that is a ramp-type chirp that increases in the frequency for a third period;

receiving, by the FMCW radar, a second signal corresponding to the first signal, the second signal comprising a first portion corresponding to the first chirp and a second portion corresponding to the second chirp;

generating, by a processing device and using the first chirp and the first portion, a third signal indicative of a human vital sign, wherein the human vital sign is a heart rate or a respiratory rate;

measuring, by the processing device, a received signal strength indicator (RSSI) value of the second portion at the frequency in a range of 55-65 GHz; and determining, by the processing device and using the RSSI value, a value indicative of oxygen-concentration in an ambient environment of the device.

9. The method of claim 8, further comprising:

determining that the value is less than a first threshold value corresponding to a first percentage of the oxygen-concentration in the ambient environment; and providing an alert.

10. The method of claim 8, the method further comprising:

determining that the RSSI value is less than a RSSI threshold value associated with a first percentage of the oxygen-concentration in the ambient environment; and providing an alert.

11. The method of claim 8, further comprising:

determining that the RSSI value is less than a first RSSI threshold value associated with a first percentage of the oxygen-concentration;

providing a first alert;

sending a fourth signal having a third chirp having the triangular-type shape and a fourth chirp having the ramp-type chirp, wherein the fourth signal is in the millimeter wave (mmWave) frequency range;

receiving a fifth signal corresponding to the fourth signal, the fifth signal comprising a third portion corresponding to the third chirp and a fourth portion corresponding to the fourth chirp;

determining a second RSSI value of the fourth portion at the frequency in the range of 55-65 GHz;

determining that the second RSSI value is less than a second RSSI threshold value associated with a second percentage of the oxygen-concentration, wherein the second RSSI threshold value is less than the first RSSI threshold value; and providing a second alert, wherein the second alert and the first alert are of different types.

12. The method of claim 8, further comprising:

sending a fourth signal having the sequence of chirps comprising a third chirp that is the triangular-type chirp that increases in the frequency for a fourth period and decreases in the frequency for a fifth period and a fourth chirp that is the ramp-type chirp that increases in the frequency for a sixth period, wherein the fourth period is different than the first period;

receiving a fifth signal corresponding to the fourth signal, the fifth signal comprising a third portion corresponding to the third chirp and a fourth portion corresponding to the fourth chirp;

generating, using the third chirp and the third portion, a sixth signal indicative of the human vital sign;

measuring a second RSSI value of the second portion at the frequency in the range of 55-65 GHz; and determining, using the second RSSI value, a second value indicative of the oxygen-concentration in the ambient environment of the device.

13. The method of claim 8, further comprising:

sending a fourth signal having the sequence of chirps comprising a third chirp that is the triangular-type chirp that increases in the frequency for a fourth period and decreases in the frequency for a fifth period and a fourth chirp that is the ramp-type chirp that increases in the frequency for a sixth period, wherein the fourth chirp increases in the frequency to a frequency higher than the second chirp;

receiving a fifth signal corresponding to the fourth signal, the fifth signal comprising a third portion corresponding to the third chirp and a fourth portion corresponding to the fourth chirp;

generating, and using the third chirp and the third portion, a sixth signal indicative of the human vital sign;

measuring a second RSSI value of the second portion at the frequency in the range of 55-65 GHz; and determining, using the second RSSI value, a second value indicative of the oxygen-concentration in the ambient environment of the device.

14. The method of claim 8, wherein the first chirp increases in the frequency from a first time to a second time and decreases in the frequency from the second time to a third time, and wherein the second chirp increases in the frequency from the third time to a fourth time.

15. The method of claim 8, wherein the first chirp has a first duration that is twice a second duration of the second chirp.

16. The method of claim 8, wherein the first chirp has a first peak frequency and the second chirp has a second peak frequency, and wherein the second peak frequency is greater than the first peak frequency.

17. A method of operating a device with a frequency-modulated continuous wave (FMCW) radar that operates in a millimeter wave (mmWave) frequency range, the method comprising:

sending a first signal having a sequence of chirps comprising a first chirp that is a triangular-type chirp that increases in frequency for a first period and decreases in the frequency for a second period and a second chirp that is a ramp-type chirp that increases in the frequency for a third period;

receiving a second signal corresponding to the first signal, the second signal comprising a first portion corresponding to the first chirp and a second portion corresponding to the second chirp;

generating, using the first chirp and the first portion, a third signal indicative of a human vital sign, wherein the human vital sign is a heart rate or a respiratory rate;

measuring a received signal strength indicator (RSSI) value of the second portion at the frequency in a range of 55-65 GHz; and determining, using the RSSI value, a value indicative of oxygen-concentration in an ambient environment of the device.

18. The method of claim 17, further comprising:

sending a fourth signal having the sequence of chirps comprising a third chirp that is the triangular-type chirp that increases in the frequency for a fourth period and decreases in the frequency for a fifth period and a fourth chirp that is the ramp-type chirp that increases in the frequency for a sixth period, wherein the fourth period is different than the first period;

receiving a fifth signal corresponding to the fourth signal, the fifth signal comprising a third portion corresponding to the third chirp and a fourth portion corresponding to the fourth chirp;

generating, using the third chirp and the third portion, a sixth signal indicative of the human vital sign;

measuring a second RSSI value of the second portion at the frequency in the range of 55-65 GHz; and determining, using the second RSSI value, a second value indicative of the oxygen-concentration in the ambient environment of the device.

19. The method of claim 17, further comprising:

sending a fourth signal having the sequence of chirps comprising a third chirp that is the triangular-type chirp that increases in the frequency for a fourth period and decreases in the frequency for a fifth period and a fourth chirp that is the ramp-type chirp that increases in the frequency for a sixth period, wherein the fourth period is different than the first period;

receiving a fifth signal corresponding to the fourth signal, the fifth signal comprising a third portion corresponding to the third chirp and a fourth portion corresponding to the fourth chirp;

generating, using the third chirp and the third portion, a sixth signal indicative of the human vital sign;

measuring a second RSSI value of the second portion at the frequency in the range of 55-65 GHz; and determining, using the second RSSI value, a second value indicative of the oxygen-concentration in the ambient environment of the device.

20. The method of claim 17, further comprising:

determining that the value is less than a first threshold value corresponding to a first percentage of the oxygen-concentration in the ambient environment; and providing an alert.

* * * * *